US012089958B2

(12) United States Patent
Elliott et al.

(10) Patent No.: US 12,089,958 B2
(45) Date of Patent: *Sep. 17, 2024

(54) PERSONAL HEALTH DATA COLLECTION

(71) Applicant: LMD IP, LLC, Oklahoma City, OK (US)

(72) Inventors: Christopher Elliott, St Sulpice (CH); Mark-Eric Jones, Vaud (CH); Mikhail Nagoga, Pully (CH); Shady Gawad, Lonay (CH); Mark Bennett, Godalming (GB)

(73) Assignee: LMD IP, LLC, Oklahoma City, OK (US)

( * ) Notice: Subject to any disclaimer, the term of this patent is extended or adjusted under 35 U.S.C. 154(b) by 84 days.

This patent is subject to a terminal disclaimer.

(21) Appl. No.: 17/847,296

(22) Filed: Jun. 23, 2022

(65) Prior Publication Data

US 2022/0395231 A1 Dec. 15, 2022

Related U.S. Application Data

(63) Continuation of application No. 15/536,390, filed as application No. PCT/EP2015/079888 on Dec. 15, 2015, now Pat. No. 11,412,987.

(30) Foreign Application Priority Data

Dec. 16, 2014 (GB) ...................................... 1422405
Feb. 23, 2015 (GB) ...................................... 1502989

(51) Int. Cl.
A61B 5/00 (2006.01)
A61B 5/022 (2006.01)
(Continued)

(52) U.S. Cl.
CPC ............ *A61B 5/6898* (2013.01); *A61B 5/022* (2013.01); *A61B 5/02241* (2013.01);
(Continued)

(58) Field of Classification Search
CPC ...... A61B 5/022; A61B 5/0261; A61B 5/0295
See application file for complete search history.

(56) References Cited

U.S. PATENT DOCUMENTS 5,865,755 A 2/1999 Golub
6,475,153 B1 * 11/2002 Khair .................... A61B 5/026
600/485
(Continued)

FOREIGN PATENT DOCUMENTS

EP 2637559 A1 * 9/2013 ......... A61B 5/02035
WO 2010/017973 A1 2/2010
(Continued)

OTHER PUBLICATIONS

Karr, C. L., Stanley, D. A., & Scheiner, B. J. (1991). Genetic algorithm applied to least squares curve fitting (No. 9339). US Department of the Interior, Bureau of Mines. (Year: 1991).*
Tanaka, G., Yamakoshi, K. I., Sawada, Y., Matsumura, K., Maeda, K., Kato, Y., . . . & Ohguro, H. (2011). A novel photoplethysmography technique to derive normalized arterial stiffness as a blood pressure independent measure in the finger vascular bed. Physiological Measurement, 32(11), 1869. (Year: 2011).*
(Continued)

Primary Examiner — Keith M Raymond
Assistant Examiner — Johnathan Maynard
(74) Attorney, Agent, or Firm — Crowe & Dunlevy, P.C.

(57) ABSTRACT

The present invention provides a PHHM for the measurement of a subject's BP and, optionally, one or more other vital signs, comprising a housing located on a PHHCD or a hand-held component of a computing system; a blood flow
(Continued)

occlusion means located in the housing such that, when the housing is located on the PHHCD or the hand-held component, an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHCD or computing system is adapted to process signals acquired by the pressure sensor and the blood flow detecting means to provide at least a measurement of the BP of a subject, the processor is further adapted to carry out a process to measure a DBP value and a SBP value, the DBP and the SBP values are estimated in such a way that the difference between the measured optical signals and those that would be generated by the estimation of the DBP and SBP values is minimized or the DBP and the SBP values are estimated in such a way that the difference between the measured incremental pressure signals and those that would be generated by the estimation of the DBP and SBP values is minimized. The present invention also provides alternative PHHMs and SADs for use in such PHMS.

12 Claims, 18 Drawing Sheets

(51) Int. Cl.
A61B 5/026 (2006.01)
A61B 5/0295 (2006.01)
A61B 5/1455 (2006.01)
A61B 5/024 (2006.01)
A61B 5/0245 (2006.01)

(52) U.S. Cl.
CPC .......... *A61B 5/0261* (2013.01); *A61B 5/0295* (2013.01); *A61B 5/14551* (2013.01); *A61B 5/6826* (2013.01); *A61B 5/02438* (2013.01); *A61B 5/0245* (2013.01); *A61B 5/14552* (2013.01); *A61B 2560/0228* (2013.01); *A61B 2560/0406* (2013.01); *A61B 2560/0425* (2013.01); *A61B 2560/0462* (2013.01); *A61B 2560/0468* (2013.01)

(56) References Cited

U.S. PATENT DOCUMENTS

| | | | | |
|---|---|---|---|---|
| 2010/0160797 | A1* | 6/2010 | Banet | A61B 5/02416 600/509 |
| 2011/0105918 | A1* | 5/2011 | Fortin | A61B 5/7203 600/493 |
| 2011/0125034 | A1* | 5/2011 | Tsuji | A61B 8/0891 600/485 |
| 2011/0166461 | A1* | 7/2011 | Susstrunk | A61B 5/02225 600/494 |
| 2014/0024905 | A1* | 1/2014 | Sarrafzadeh | A61B 5/7271 600/328 |
| 2015/0051500 | A1* | 2/2015 | Elliott | A61B 5/1455 600/491 |
| 2016/0262695 | A1* | 9/2016 | Zhang | A61B 5/7278 |
| 2017/0354331 | A1* | 12/2017 | Borkholder | G09B 23/30 |

FOREIGN PATENT DOCUMENTS

| | | | | |
|---|---|---|---|---|
| WO | 2012/064326 A1 | 5/2012 | | |
| WO | WO-2013001265 A2 * | 1/2013 | ......... | A61B 5/02055 |
| WO | WO-2014125431 A1 * | 8/2014 | ........... | A61B 5/0205 |

OTHER PUBLICATIONS

Lee, C., Shin, H. S., & Lee, M. (2011). Relations between ac-dc components and optical path length in photoplethysmography. Journal of biomedical optics, 16(7), 077012. (Year: 2011).*
Drzewiecki et al., "Theory of the oscillometric maximum and the systolic and diastolic detection ratios", Annals of Biomedical Engineering, 1994, 22, 88-96.
Karr et al., "Genetic algorithm applied to least squares curve fitting (No. 9339)", US Department of the Interior, Bureau of Mines, Year: 1991.
Langeworters et al., "Pressure-diameter relationships of segments of human finger arteries", Clin. Phys. Physiol. Meas., 1986, 7, 43-55.
Lee et al., "Relations between ac-dc components and optical path length in photoplethysmography", Journal of biomedical optics, 2011, 16(7), 077012.
Padilla J., et al., "Pulse wave velocity and digital volume pulse as indirect estimators of BP: pilot study on healthy volunteers", Cardiovasc. Eng., 2009, 9, 104-112.
Stergiopolus et al., "Physical basis of pressure transfer from periphery to aorta: a model-based study", Am. J. Physiol., 1998, 274, H1386-H1392.
Tanaka, et al., "A novel photoplethysmography technique to derive normalized arterial stiffness as a blood pressure independent measure in the finger vascular bed", Physiological Measurement, 2011, 32(11), 1869.

* cited by examiner

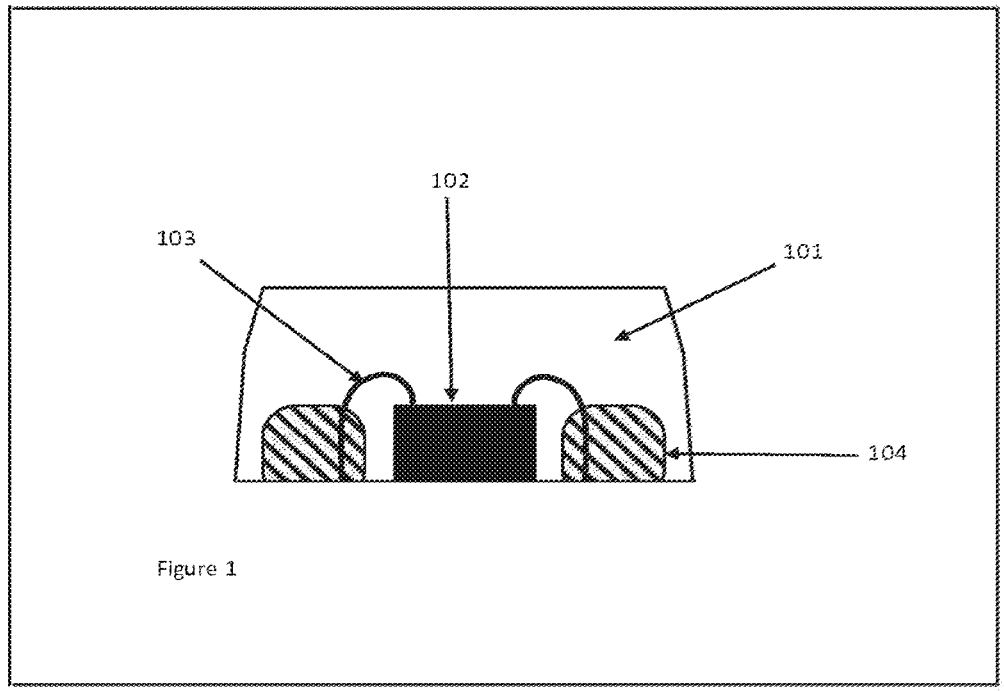
Figure 1
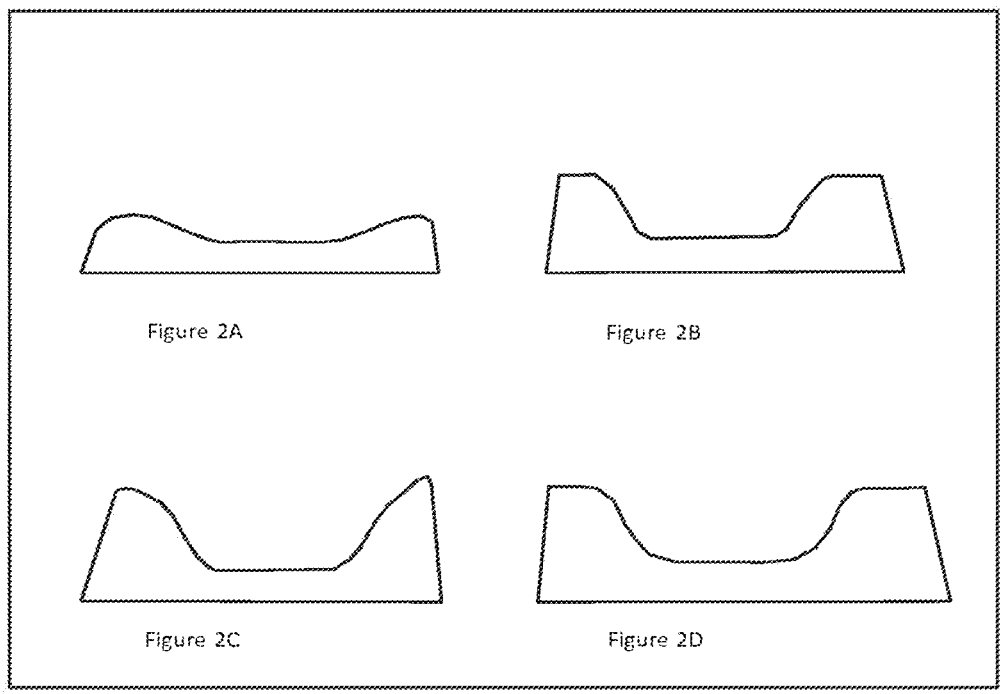
Figure 2A
Figure 2B
Figure 2C
Figure 2D

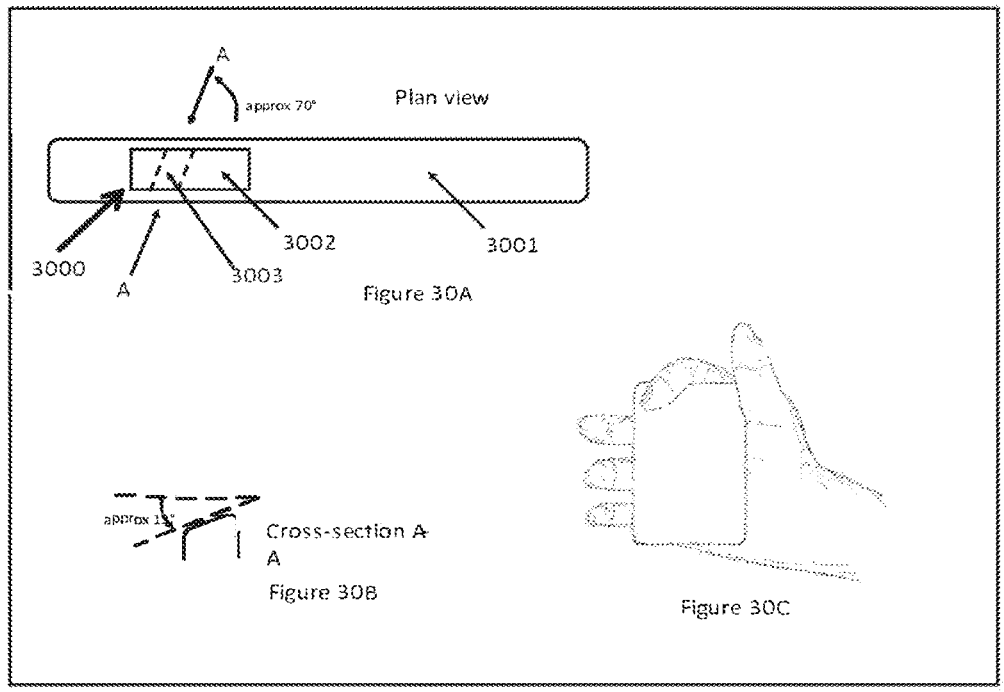
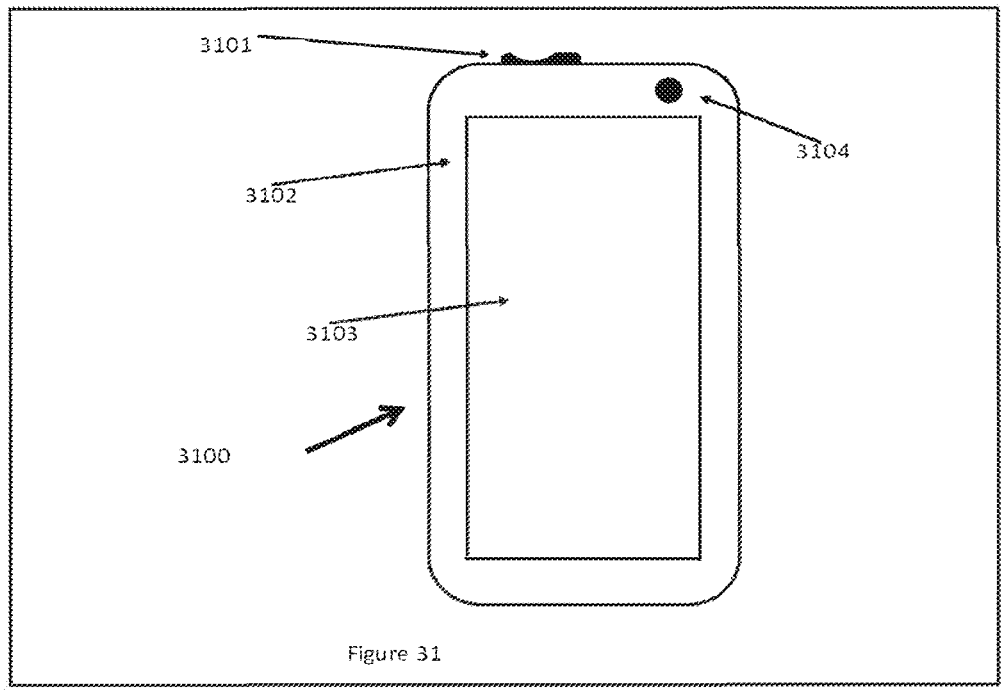

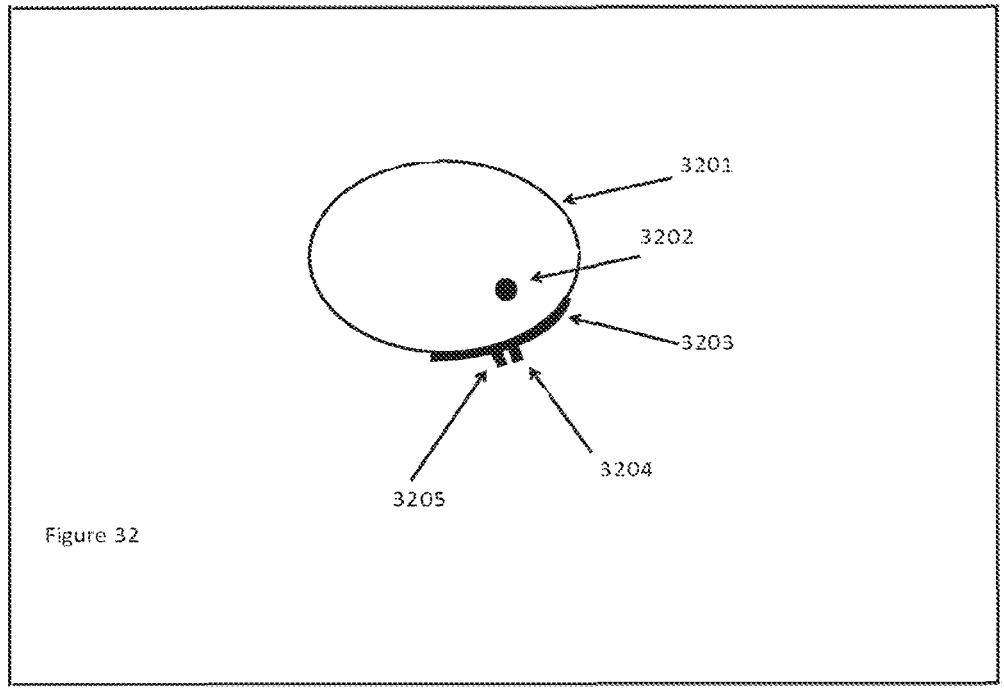
Figure 32
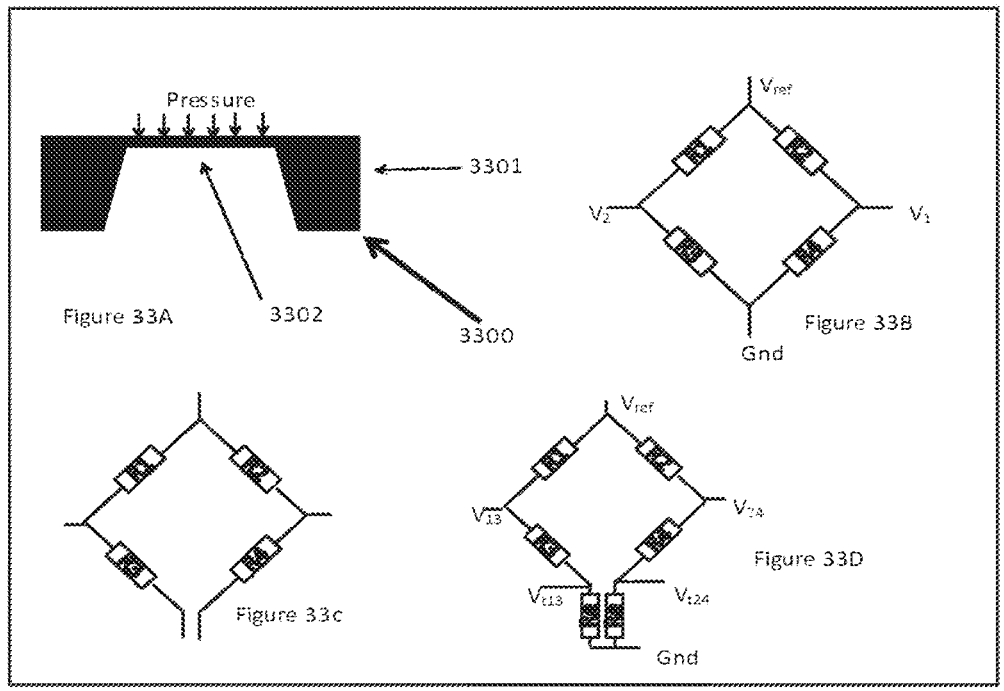
Figure 33A
Figure 33B
Figure 33C
Figure 33D

PERSONAL HEALTH DATA COLLECTION

CROSS-REFERENCE TO RELATED APPLICATIONS

This application is a Continuation of U.S. application Ser. No. 15/536,390, filed Jun. 15, 2017, which is a U.S. National Stage application of International Patent Application No. PCT/EP2015/079888, filed Dec. 15, 2015, which claims the benefit of United Kingdom Patent Application No. 1422405.9, filed Dec. 16, 2014, and United Kingdom Patent Application No. 1502989.5, filed Feb. 23, 2015, the disclosures of which are each hereby incorporated by reference for any and all purposes as if set forth in their entireties herein.

FIELD OF THE INVENTION

The present invention relates to a device for collecting personal health data when the device is in contact with a body part of a subject or vice versa.

In particular, the invention relates to a signal acquisition device for acquiring signals which can be used to derive one or more measurements of a parameter related to the health of a user. The invention also relates to a personal hand-held monitor comprising such a signal acquisition device, a holder for transferring a signal acquisition device, a socket adapted to hold a signal acquisition device a method for calibrating a signal acquisition device and a protective cover for a personal hand-held monitor.

Abbreviations

In the present specification, the following abbreviations are used. Their meanings are given after the abbreviation: PHHM—personal hand-held monitor; PHHCD—personal hand-held computing device; PPG—photoplethysmography or photoplethysmographic; SAD—signal acquisition device; BP—blood pressure; DBP—diastolic blood pressure; SBP—systolic blood pressure; PDA—personal digital assistant device; TV—television; ASIC—Application Specific Integrated Circuit; MEMS—Micro-Electro-Mechanical System; PCB—printed circuit board; CTO—coefficient of temperature offset; and LED—light emitting diode.

The term "subject" refers to the person whose personal health data is being collected. The term "user" refers to the person who is using a PHHM to collect personal health data. The user may be the subject or may be another person, such as a healthcare professional, family member or friend who uses or assists the subject to use the PHHM to collect the subject's personal health data.

BACKGROUND OF THE INVENTION

Mobile phones (also known as cellphones) and tablet computers as well as mice and remote controllers, such as TV remote controllers, are part of everyday life. In the developed world, a large majority of adults have or use some of these devices. There have been various proposals for using mobile telephony in healthcare. However, all these proposals have drawbacks.

WO2013/001265 discloses a large amount of background material which is also relevant to the inventions disclosed in the present application. WO2013/001265 contains background information relating to established methods of measuring blood pressure, including the Riva-Rocci ausculatory method, the automatic oscillometric method, the volume clamp method and related relative measurements. It also discloses inventions relating to the measurement of blood pressure and other health-related parameters, in particular using a specially adapted PHHCD. The disclosures in WO2013/001265 are hereby incorporated by reference in their entirety into this description.

WO2014/125431 discloses improvements and additions to the inventions disclosed in WO2013/001265. These inventions also relate to the measurement of blood pressure and other health-related parameters, in particular using a specially adapted PHHCD. The disclosures in WO2014/125431 are also hereby incorporated by reference in their entirety into this description.

SUMMARY OF THE INVENTION

The PHHMs disclosed in WO2013/001265 and WO2014/125431 address the weaknesses of the established methods in that: they provide objective, precise, repeatable, absolute and accurate results; they do not use toxic materials; they are easy to use without specialist training; and they use only inexpensive, simple and reliable technology.

The inventions disclosed in WO2013/001265 and WO2014/125431 include many advances on the previous state of the art but still have limitations. This application discloses several enhancements and refinements to the PHHMs described therein that can improve their usability, cost, effectiveness and/or ease of integration with the PHHCD.

There are several aspects to the present invention. For convenience, they are described separately but, as is apparent to a person skilled in the art, they may be used cooperatively to create a unified device in which the various aspects work cooperatively to share data and/or enhance their mutual performance and/or reduce costs and complexity. It will also be appreciated that the aspects of the present invention described below can be used together in any combination of two or more of the aspects, in particular for the purposes set out in the Table on page 43 of WO2014/125431 and may be used in combination with the features described in connection with either or both of WO2013/001265 and WO2014/125431.

For convenience, the description herein describes the body part as a finger, but it will be apparent to a person skilled in the art that the device may be applied to other body parts.

The invention disclosed herein draws on many of the disclosures of WO2013/001265 and WO2014/125431 and distinguishes between a SAD and a processor. The SAD incorporates the sensors and means for signal conditioning and for receiving and transmitting data but carries out no processing. All processing is carried out by a PHHCD or computing system to which the SAD is attached. This transformation affects both the SAD and the processor. It allows improvements to the design, construction and operation of the SAD and also allows each SAD to be calibrated during production in a way that is more amenable to automation. The PHHCD or computing system allows sophisticated data processing and use of complex algorithms to extract estimates of health-related parameters. The computing power and pre-existing capabilities of the PHHCD or computing system may be used to provide user-friendly, interactive controls and displays and to exploit the data obtainable from more complex sensors than would be possible with simpler processors.

First Aspect of the Present Invention—SAD with Gel Sensor

In a first aspect, the present invention provides a SAD for acquiring signals which can be used to derive a measurement of a subject's BP and, optionally, one or more other vital signs, the SAD comprising a housing adapted to be located on a PHHCD or a hand-held component of a computing system; a flexible and essentially incompressible gel located in the housing such that, when the housing is located on the PHHCD or the hand-held component, an open surface of the gel is available to be pressed against a body part of the subject or to have a body part of the subject pressed against it; a pressure sensor embedded in the flexible and essentially incompressible gel, which sensor is adapted to provide an electrical signal indicative of the pressure applied to or by the open surface; means for detecting the flow of blood in the body part of the subject when pressure is applied to or by the open surface, the blood flow detecting means being located on the housing or in the flexible and essentially incompressible gel; and receiving and transmitting means for receiving electrical signals from the pressure sensor and the blood flow detecting means and for transmitting electrical signals indicative of the pressure and blood flow to the processor of the PHHCD or computing system.

Preferably, the open surface of the gel is saddle-shaped. Preferably, the open surface of the gel is shaped such that, when the SAD is located on the PHHCD or the hand-held component of the computing system, the longitudinal axis extending through the centre of the valleys of the saddle is located at an angle to the longer axis of the surface of the PHHCD or hand-held component in which the SAD is located.

Second Aspect of the Present Invention—SAD with Saddle-Shaped Sensor

According to a second aspect of the invention, there is provided a SAD for acquiring signals which can be used to derive a measurement of a subject's BP and, optionally, one or more other vital signs, the SAD comprising: a housing adapted to be located on a PHHCD or a hand-held component of a computing system; a pressure sensing means located in the housing such that, when the housing is located on the PHHCD or the hand-held component, an open surface of the sensing means is available to be pressed against a body part of the subject or to have a body part of the subject pressed against it; a pressure sensor in the pressure sensing means, which sensor is adapted to provide an electrical signal indicative of the pressure applied to or by the open surface, a means for detecting the flow of blood through the body part of the subject when pressure is applied to or by the open surface; means for receiving electrical signals from the pressure sensor and the blood flow detecting means and for transmitting electrical signals indicative of the pressure and blood flow to the processor of the PHHCD or computing system, wherein the open surface is saddle-shaped such that, when the SAD is located on the PHHCD or the component of the computing system, the longitudinal axis extending through the centre of the valleys of the saddle is located at an angle to the longer axis of the surface of the PHHCD or hand-held component in which the SAD is located.

Preferably, in the SAD of the second aspect of the invention, the pressure sensing means comprises a flexible and essentially incompressible gel in which is embedded a pressure sensor, as defined for the SAD of the first aspect of the invention.

Pressing the open surface of the pressure sensing means of the second aspect of the invention or the open surface of the flexible and essentially incompressible gel of the first aspect of the invention or the preferred form of the second aspect of the invention against a part of a body or pressing a part of a body against the open surface causes occlusion of blood vessels in the body part and so the open surface is a blood flow occlusion means as the term is used in WO2013/001265 and WO2014/125431.

Preferably, where the SAD of either of the first two aspects comprises a flexible and essentially incompressible gel, the housing of the SAD includes a well in which the flexible and essentially incompressible gel is located and the open surface of the gel is at the open end of the well.

Gel materials are effective but some can be difficult to handle and manufacture and may not have long-term stability. In order to overcome the disadvantages of some gels, preferably the gel comprises a rubber-like material which has a bulk modulus which is larger by a factor of at least 10 than its shear and Young's moduli and whose bulk modulus is smaller by a factor of at least 10 than the bulk modulus of the material used to form the housing. Preferably, the gel has a Durometer, on the Shore A scale at 25° C., of from 50 to 70, more preferably from 55 to 65. Such a gel is effective and does not suffer from the disadvantages referred to above.

Suitable gels may be made from: a flexible epoxy resin, such as a resin formed from EPICOL 295, a 2-component system for making a soft epoxy resin including a modified epoxy resin and a modified amine hardener, supplier by APM Technica; or a cured silicone resin, such as a cured silicone resin formed from Dow Corning Sylgard 160, a 2-component system for making a soft silicone resin including a silicone resin and a catalyst.

The flexible and essentially incompressible gel in the well of the SAD may comprise at least two layers made of different materials. The at least two layers made of different materials may comprise at least a first layer which abuts the bottom of the well and a second layer which provides the open surface of the gel. Preferably, the second layer of the gel is adapted to resist physical or chemical damage and the first layer has lower, by a factor of at least 10, shear strength than that of the second layer or is a liquid, such as an oil. The pressure sensor may be embedded in the first layer. Alternatively, the first layer may be a hard material, such as the same material as is used to form the housing.

The open surface of the flexible and essentially incompressible gel may be covered by a flexible membrane forming some or all of its surface.

Where the SAD comprises a gel located in a well, the well containing the pressure sensor has to be substantially larger than the pressure sensor itself in order to accommodate the connections, known as wire bonds, that reach from the top of the pressure sensor to the PCB on which it is mounted.

Where the pressure sensor is mounted on the surface of the PCB, its open surface is up to 0.5 mm above the surface of the PCB. When the gel that fills the volume around the pressure sensor expands, it flows upwards towards the open surface and causes a region of reduced pressure above the pressure-sensing surface of the pressure sensor. This causes an apparent change of pressure.

This change may be measured during calibration (see below) and compensated by algorithms that estimate the temperature of the gel by measuring the resistance of the pressure sensor and applying a correction proportional to the temperature change.

This is effective but preferably the magnitude of the correction should be reduced in order to reduce the effect of any errors in that correction. In order to achieve this, it is preferred that a material with the smallest convenient coefficient of thermal expansion (CTE) is provided within the relevant part of the well. For instance, as shown in FIG. 1, which shows a cross-section of the well for a typical embodiment of the device, the gel (101) contains the pressure sensor (102) and its wire bonds (103). A wall (104) of material with a relatively low CTE is deposited around the pressure sensor. Preferably, the material is made from: a heat curable epoxy adhesive and encapsulant, such as Hysol FP4451 TD, a damming material that is designed as a flow control barrier around areas of bare chip encapsulation; or a single component UV curable epoxy adhesive and encapsulant, such as Epotek OG116-31. Such materials are flexible when applied and have a low CTE when hardened. They also become very strong and help to stiffen the PCB on which the pressure sensor is mounted, thus reducing the risk that deformations of the PCB will distort the pressure sensor and cause erroneous readings.

Preferably, where the open surface is saddle-shaped, the longitudinal axis of the saddle-shaped open surface is, in use, located at an angle of about 70° to the longer axis of the surface of the PHHCD or hand-held component in which the SAD is located.

Preferably, the longitudinal axis of the saddle-shaped open surface is, in use, located at an angle of about 15° to the plane of the surface of the PHHCD or hand-held component in which the SAD is located.

The radius of curvature of the saddle-shaped surface may be approximately the same as the radius of curvature of the body part with which it is to interact. An open surface with this shape is shown in FIG. 2A of the accompanying drawings.

Preferably, the shape of the open surface is adapted to contain an artery within the body part and to create a more homogeneous pressure field. It has been found by analysis and trials that raising the sides of the saddle-shaped open surface can give more accurate and reliable measurements of blood pressure. FIGS. 2B and 2C show two shapes that were tested on a finger. FIG. 2D shows a compromise shape that is preferred. The shapes are asymmetric to accommodate the electronic and optical components and all have a flat region in the centre to allow pressure to be measured without creating curvature in the skin. FIG. 3 is copied from a Magnetic Resonance Image of a finger with an open surface having the shape shown in FIG. 2C pressed against it. The artery 304 embedded in tissue 302 is held between, on one side, the bone 301 and cartilage 303 and, on the other side, the indentations 305 formed by the saddle-shaped open surface.

Third Aspect of the Invention—Pressure Sensor

WO2013/001265 and WO2014/125431 and the description of the SADs above refer to the use of pressure sensors for measuring the pressure between the blood flow occlusion means, such as a button or an open surface, such as of a gel, and the body part, such as a finger. These may be conventional pressure sensors. Such conventional pressure sensors have the advantage that they are robust and easy to fabricate. However, conventional pressure sensors may suffer from drift, for instance if the properties of the gel or incompressible fluid change, and may suffer from the disadvantage that any practicable force sensor deflects when the force is applied so the surface, for instance of the button, does not remain coplanar with its surround.

Therefore, according to a third aspect of the present invention, in a SAD according to either of the first two aspects of the invention, the pressure sensor comprises a magnetic actuator adapted to maintain the surface of the blood flow occlusion means with which the body part is to come into contact at a constant position.

This aspect of the present invention also includes a PHHM for the measurement of a subject's BP and, optionally, one or more other vital signs, comprising a housing located on a PHHCD or a hand-held component of a computing system; a blood flow occlusion means located in the housing such that an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHCD or computing system is adapted to process signals acquired by the pressure sensor and the blood flow detecting means to provide at least a measurement of the BP of a subject, wherein the pressure sensor comprises a magnetic actuator adapted to maintain the open surface of the blood flow occlusion means with which the body part is to come into contact at a constant position.

The PHHM may be a PHHM as described in either of WO2013/001265 and WO2014/125431 or a PHHM comprising a SAD according to the first or second aspect of the present invention.

The use of a pressure sensor of this aspect of this invention overcomes the above-mentioned limitations by balancing the force between the open surface and the body part with an electromagnetic force. The electrical power required to maintain the open surface in position can be measured and processed to provide a measure of the pressure between the open surface and the body part.

FIG. 4 shows an embodiment of this aspect of the present invention. The button 401 has attached to it a rod 403 of ferromagnetic material. A coil 402 of conducting wire surrounds the rod 403. The rod 403 slides in the coil 402.

Alternatively, the ferromagnetic material may be replaced wholly or in part by a permanent magnet.

Alternatively, the rod may be split so that one part of it is attached to the button and the other to the coil, and each part may be made of a ferromagnetic material, a permanent magnet or a non-magnetic material. Alternatively, a second coil may be employed instead of the ferromagnetic material or permanent magnet.

In use, the current through the coil(s) is continuously adjusted by an electronic circuit (not shown) to balance the force on the button and ensure that the button remains in the same position. This requires only a low bandwidth, typically less than 20 Hz, and the design of such a circuit will be obvious to a person skilled in the art. The force generated by the current is equal to the force on the button and the pressure on the button is found by dividing the force by the area of the button.

Preferably, the position of the button is found by measuring the inductance of the coil or the mutual inductance between the two coils if such are employed. Preferably, said inductance is found by adding a parallel capacitor to the coil(s) and measuring the resonant frequency. The resonant frequency may be chosen to allow the electronic circuit simultaneously to measure the resonant frequency and to balance the force on the button. A frequency in excess of 100 KHz is suitable.

The rod may be located by means of a sliding surface within the coil. Alternatively, the button may be retained by a thin ring of soft adhesive between the button and its surround. This has the advantage of reducing friction and provides a water- and dust-proof seal.

Alternatively, a proximity sensor may be used to measure the position of the button. The proximity sensor may be optical, capacitative or magnetic.

Preferred Features of the SAD of any Aspect of the Present Invention

Preferably, the blood flow detection means of the SAD comprises at least one infra-red and visible LED and at least one photo-detector, wherein the at least one infra-red and visible LED and the at least one photo-detector are connected to the means for receiving and transmitting the electrical signals. Optionally, the at least one infra-red and visible LED and the at least one photo-detector are embedded in the flexible and essentially incompressible gel such that light can be transmitted and received through the open surface. The or each infra-red and visible LED and the or each photo-detector each may include a transparent window that permits transmission and reception, respectively, of infra-red and visible light.

Preferably, the SAD further comprises a bolometric temperature sensor, wherein the bolometric temperature sensor is connected to the means for receiving and transmitting electrical signals.

Preferably, the receiving and transmitting means is adapted to receive from the processor and transmit to it at least the pressure sensor and the blood flow sensor control signals.

The receiving and transmitting means may comprise an ASIC. The ASIC may include electronic circuitry associated with the sensor(s) in the SAD.

Preferably, the housing comprises two longitudinal slots adapted to mount the SAD in a mounting guide in the PHHCD or the hand-held component of the computing system. The mounting guide may be adapted to provide electrical connections to the SAD.

In using a SAD of either of the first two aspects of the present invention, pressing the open surface against a body part of the subject, such as a finger, or vice versa, creates a pressure within the body part of the subject. The pressure sensor measures, directly or indirectly, the pressure between the open surface and the body part of the subject.

As explained below, provided that the open surface and the body part of the subject are in contact for a sufficient period of time and the pressure between the open surface and the body part of the subject is varied sufficiently, the processor of the PHHCD or the computing system can analyse the signals received over a period of time and varying over a range of pressures to determine the SBP and/or DBP of the subject. It has been found that it is possible to fit the signals received from the pressure sensor, in whatever order they are received, to a curve from which SBP and/or DBP can be determined.

Preferably, the pressure sensor of the SAD is a MEMS pressure sensor which comprises a membrane and four resistive elements within the membrane, wherein the MEMS is adapted to: be embedded in the gel that is adapted to be pressed against the body part of the subject or to have the body part of the subject pressed against it; perform four voltage measurements in order to obtain the instantaneous resistances of said four resistive elements; and estimate, based on the instantaneous resistances, the temperature of the membrane, the average pressure to which the membrane is subject and the orientation and magnitude of the pressure gradient across the pressure sensors of the MEMS.

Preferably, the four resistive elements are constructed to minimize the coupling between them.

Preferably, each SAD of the present invention has a unique, unalterable electronically-readable identifier. This may be provided during manufacture or testing and should be readable by the PHHCD or computing system once the SAD is located in operative position. Calibration data can then be downloaded to the processor of the PHHCD or the computing system based on this unique identifier.

The blood flow sensor may comprise an optical sensor that provides an electrical signal related to the luminal area of the artery by means of the absorption of light. It draws on the experience of pulse oximeters using PPG. Such pulse oximeters have been on the market since the 1980s. They are used to estimate the degree of oxygenation in arterial blood. The same principles as are described in the disclosures in WO2013/001265 and WO2014/125431 apply equally to all the aspects of the present invention. Red and infra-red light is transmitted by one or more photo-emitters towards a body part of the subject and detected by one or more photo-detectors after the light has passed through or been reflected by the body part of the subject. The infra-red light is more strongly absorbed by oxygenated blood than by non-oxygenated blood (a suitable wavelength is 940 nm); the red light is more strongly absorbed by non-oxygenated blood than by oxygenated blood (a suitable wavelength is 660 nm). The ratio of the fractional changes in red and infra-red intensity is monotonically related to the percentage of oxygenation of the blood. It is also possible to use green light (a suitable wavelength is 520 nm) in place of or as well as the red or infra-red light.

Infra-red light is preferentially absorbed by oxygenated haemoglobin so the amount of absorption is approximately proportional to the amount of arterial blood through which the light passes. For a given length of artery, the amount of arterial blood is proportional to the luminal area of the artery and therefore the absorption signal is also approximately proportional to the luminal area. As the artery expands on each systole and contracts on diastole, the absorption of infra-red light varies with the pulse.

The SADs may include two LEDs used both to detect the flow of blood for pressure measurement and as part of a pulse oximeter to estimate blood oxygen concentration ($SpO_2$). The principles of the pulse oximeter are well-known to persons skilled in the art and are described in the previous applications.

It is possible to purchase LEDs for which the central emission wavelength is controlled to around ±2 nm so as to ensure an accurate measurement of $SpO_2$. However, these are expensive and the aim of the disclosed inventions is to reduce size and cost to a level at which the SAD integrated with a PHHCD can become ubiquitous and personal to the user. Preferably, the SADs according to the above aspects of the present invention use less expensive LEDs for which the central emission wavelength is controlled to around ±10 nm. Such LEDs may also be used in the PHHMs of the two previous applications. In order to allow this to occur, the processing means of the PHHCD or the computer system is adapted to download calibration data related to the LEDs used in the SAD or PHHM and the calibration data are used to compensate for the broader range of possible central emission wavelengths.

The required calibration data may be obtained using a holder and calibration system as described in further detail below.

The SAD may include an electrical sensor comprising an electrode disposed on or adjacent the open surface. The electrode may be formed of a conducting material on the surface of the housing or the housing may be made of an electrically conducting material and the SAD may include at least one electrically conductive pad in contact with the conductive material, wherein the conductive pad is adapted to conduct electrical signals from said conductive material to the receiving and transmitting means. The electrode may be adapted to transmit electrical signals from the body part of the subject pressed against the open surface to the receiving and transmitting means within the SAD. Preferably, the open surface is constructed with a surface that gives a good electrical connection, such as an array of micro-pyramids.

Preferably, the receiving and transmitting means is adapted to amplify the signals from the electrical sensor and, if desired, to filter the signals before, during or after amplification. An amplified and filtered signal produced by the receiving and transmitting means will generally have the form shown in FIG. 5 in the attached drawings where the x axis represents time and the y axis represents potential difference. The arrows in FIG. 5 indicate the times at which the electrical signal stimulates the heart to initiate systole.

Preferably, the receiving and transmitting means is adapted to carry out signal conditioning, such as filtering, analog to digital conversion and signal amplification, in any order.

The SAD may comprise a number of separate electronic devices which are preferably integrated into a single package. However, advantageously, some or all of the electronic devices are integrated into a single unit. Such integration will bring several benefits, including reduced cost, improved reliability, reduced size and mass and reduced power consumption. Preferably, the receiving and transmitting means is adapted to cause the photo-emitter(s), when present, to be switched so that a single multiplexed photo-detector can detect light at the selected wavelengths. Preferably, the receiving and transmitting means is adapted to allow an electrical signal to be acquired from the photo-detector(s) for a period in which no light is emitted from the photo-emitter(s) to allow a further calibration of the signals.

The SAD of any of the previous aspects of the present invention may further include any of the features of the signal acquisition devices described in WO2013/001265 and WO2014/125431, for instance the module shown in FIG. 24 of WO2014/125431.

Fourth Aspect of the Present Invention—Analysis of Data

According to a fourth aspect of the invention, there is provided a PHHM for the measurement of a subject's BP and, optionally, one or more other vital signs, comprising a housing located on a PHHCD or a hand-held component of a computing system; a blood flow occlusion means located in the housing such that an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHCD or computing system is adapted to process signals acquired by the pressure sensor and the blood flow detecting means to provide at least a measurement of the BP of a subject, and wherein the processor is adapted to analyse the data as described below.

The PHHM may be a PHHM as described in either of WO2013/001265 and WO2014/125431 or a PHHM comprising a SAD according to the first or second aspect of the present invention.

Preferably, the PHHM is of such a size and weight that it can readily be manipulated by a subject using one hand to hold it against a finger of the other hand to make a measurement or by a medical practitioner holding it against the subject. The PHHM may comprise a SAD as explained above. The SAD is located on a PHHCD or a hand-held component of a computing system. Electrical signals are transmitted from the receiving and transmitting means comprised within the SAD to a processor of the PHHCD or the computing system and vice versa. The PHHCD may be a cellphone, tablet computer or MP4 player. The computing system may be a laptop, PC or TV, in which case the SAD will be located on a hand-held component of the computing system, for example on a mouse or on a remote games or TV controller.

Preferably, the PHHCD is rectanguloid, having an upper and a lower face connected by four side faces, wherein the upper face is of sufficient area to accommodate a display means and a data entry means, the distance between the upper and lower faces is small enough to be located on the subject's body part and the blood flow occlusion means is located on one of the side faces. The PHHCD may have a width of from 5 to 20 cm, a length of from 10 to 30 cm and a depth of from 0.5 to 2.0 cm. The PHHCD may have rounded corners and edges.

The signals from the receiving and transmitting means are transmitted to the processor of the PHHM. The processor of the PHHM provides high level processing that permits the calculation of the subject's BP and, optionally, one or more other vital signs. The processor may also transmit control signals to the receiving and transmitting means.

The processor may be adapted to carry out signal conditioning if the receiving and transmitting means is not adapted to do this or to carry out further signal conditioning if the receiving and transmitting means is adapted to carry out signal conditioning.

Filtering and/or conditioning may be carried out before, during or after amplification.

Preferably, the processor is adapted to:
  control and receive electrical signals from the sensor(s) in the SAD, i.e. pressure sensor, blood flow sensor, etc.
  analyze the electrical signals from the sensor(s) in the SAD in order to determine the subject's BP and, preferably, other diagnostic information; or
  control the display means of the PHHCD or computing system of the PHHM, if present, for communicating the result of the measurement to the subject.

The processor may also be adapted to receive and process electrical signals from a data entry device of the PHHCD or computing system as part of the PHHM, if present.

Preferably, the PHHM includes one or more storage devices, such as a flash memory, for storing the electrical signals received from the sensor(s) of the SAD and/or input from the data entry device of the PHHCD or computing system and any electrical signals derived from the received signals. In particular, a storage device is preferably provided for storing the subject's historical BP data derived by the processor.

The processor may also be adapted to communicate with a remote computing system, preferably wirelessly via the internet, to allow the output of the processor to be further analysed, archived and/or communicated.

Preferably, the processor is adapted to provide audible or visual instructions to the user, advantageously via the display means of the PHHCD or computing system of the PHHM, if present, to enable the user to use the PHHM optimally. This may include instructions to vary the force applied to the body part of the subject to cover a wide enough range of pressures to give a good fit to the mathematical equations shown below. For instance, if the blood flow occlusion means has not been pressed hard enough against the body part of the subject to occlude completely an artery during a systole, the PHHM may be programmed to issue via the display means of the PHHCD or computing system an instruction to the user to press harder on the blood flow occlusion means (or vice versa) so that the required electrical signals can be acquired. In this case, it is preferred that the processor is adapted so that the instructions are interactive and based on signals received from the sensor(s) in the SAD which can be used to determine whether the PHHM is in the best position or being used correctly.

The PHHCD or the computing system of the PHHM may also include: a display means for displaying measurements of the subject's SBP and/or DBP; and/or communications means for transmitting the measurements of the subject's SBP and/or DBP; and/or storage means for storing the measurements of the subject's SBP and/or DBP. If present, the storage means may also store other data sent to or generated by the processor.

The PHHCD or the computing system of the PHHM may also include a data entry device adapted to be operated by the user so that the user can enter information into the device. The data entry device may be a keypad or a touchscreen. The data entry device may be used to input data for identifying a subject so that different subjects can use the device. The data that may be entered by use of the data entry means may include, but are not restricted to, the subject's height, weight, waist circumference, finger diameter and age.

The PHHM may be operated by holding the blood flow occlusion means against a body part of the subject, such as a finger, or holding the body part of the subject against the blood flow occlusion means and varying the force exerted by the user on the blood flow occlusion means or exerted by the blood flow occlusion means on the body part of the subject to achieve a range of pressures in the body part of the subject from below DBP to above SBP. While the force of interaction between the body part of the subject and the blood flow occlusion means is being varied, the sensor(s) in the PHHM are switched on and the electrical signals generated by these sensor(s) are received and processed by the processor.

Unlike conventional sphygmomanometry, blood flow may be detected at a range of pressures in any order and the data fitted to a mathematical equation.

The waveforms of typical electrical signals received from optical, pressure and electrical sensors are shown in FIG. 6 in the attached drawings. Preferably, the primary signals that the processor extracts from these waveforms are the change in absorption on systole (from the optical sensor) and the instantaneous measured pressure at systole and diastole (from the pressure sensor). From these, the processor may be adapted to compute an estimate of the change in the optical signal as a function of pressure. Preferably, the processor is adapted to use the timing of events detected by the electrical sensor to determine the time or times at which to detect events in the optical and pressure signals.

The PHHM may be adapted to provide a measurement of other vital signs.

Preferably, the processor of the PHHCD or the computing system correlates the signals received from the pressure sensor with the signals received from the blood flow detector so that the pressure exerted between the open surface and the body part of the subject is correlated with the luminal area of the artery. The correlated values can then be fitted to a curve to provide measurements of the subject's SBP and/or DBP. This curve can be derived as follows.

The processor of the PHHM may be adapted to represent a decay law of pressure field with a parametric function. Preferably, the parametric function is an exponential.

The processor of the PHHM may be adapted to represent a decay law of optical intensity with a parametric function. Preferably, the parametric function is an exponential.

The processor of the PHHM may be adapted to integrate a plurality of contributions along an artery within the body part of the subject to calculate a total optical signal.

The processor of the PHHM may be adapted to represent the effect of respiration on BP with a parametric function.

Preferably, the processor of the PHHM is adapted to carry out a process to measure a DBP value and a SBP value, wherein the DBP and the SBP values are estimated in such a way that the difference between the measured optical signals and those that would have been generated by the estimation of DBP and SBP values is minimized. The process to estimate the DBP and SBP values may use a genetic algorithm.

The process to measure the DBP and SBP values may further comprise: calculating an initial DBP and an initial SBP value without taking account of respiration; and re-calculating the DBP and the SBP values based on an estimate of respiration and the initial DBP and the SBP values.

The processor of the PHHM may be adapted to calculate an error estimate, wherein this error estimate may be used to weight particular segments of data used for the measurement of the DBP and SBP values.

The processor of the PHHM may be adapted to obtain an estimate of the value of a parametric function which describes the stress/strain law of an artery wall, wherein this value indicates arterial health and/or age of the subject.

The change in the optical signal is known to be approximately proportional to the luminal area of the artery. The relationship between the luminal area and pressure is referred to herein as the Arterial Optical/Pressure Curve (AOPC).

It is stated in WO 2013/001265 and WO 2014/125431 that "the data from the blood flow sensor can be correlated with the signal from the pressure sensor of the blood flow occlusion means to fit the measured data to a known theoretical relationship between flow rate and pressure" (see WO2014/125431, page 13, line 13 to page 16, line 23).

The theoretical relationship can be derived entirely from considerations of the behaviour of the artery and the interaction of the body part of the subject with the open surface as described herein.

In order to explain the form of the AOPC, it is necessary to consider how the artery behaves. The relationship between luminal area and pressure is shown in FIG. 7 where TMP is the TransMural Pressure, which is the instantaneous pressure in the artery minus the External Applied Pressure (EAP), which is the pressure generated by the blood flow occlusion means and measured by the pressure sensor. Such curves have been reported by several researchers, such as Drzewiecki et al., "Theory of the oscillometric maximum and the systolic and diastolic detection ratios", Annals of Biomedical Engineering, 1994, 22, 88-96 and Langeworters et al., "Pressure-diameter relationships of segments of human finger arteries" Clin. Phys. Physiol. Meas., 1986, 7, 43-55, both using in vitro measurements of representative arteries.

Where the applied pressure is less than DBP, the artery remains open throughout the pulse cycle. The change in luminal area is approximately proportional to the electrical signal produced by the optical sensor caused by the stretching of the artery wall as the pressure difference between the inside and outside rises. Where the applied pressure is greater than DBP and less than SBP, the artery collapses during every pulse and, when open, stretches as in the previous case. When the applied pressure is greater than SBP, the artery remains closed throughout the pulse cycle. This is illustrated in FIG. 8.

The difference between the amplitude of the AOPC at DBP and SBP, corresponding to the two ends of the bars marked D S in FIG. 8, is plotted against EAP to give a curve of the form shown in FIG. 9. FIG. 9 shows a simulation for SBP=150 mmHg and DBP=80 mmHg. SBP and DBP are marked respectively by the arrows "S" and "D". FIG. 10 shows a measured version of this curve. The processing algorithms may use curve fitting routines to estimate DBP and/or SBP to high precision. In particular, there is a clearly visible transition at DBP, a feature absent from measurements made by all other non-invasive sphygmomanometers.

In practice, the measured AOPC is not perfect. It is affected by:

- the stress/strain law of the artery wall;
- the light from the at least one infra-red and visible LEDs travelling through the tissue to regions outside those in contact with the blood flow occlusion means, so being scattered from parts of the artery that are not subjected to the same pressure as the regions of the artery that are over the blood flow occlusion means;
- the change in the TMP when the artery expands and pushes back against the open surface of the blood flow occlusion means;
- the modulation of the blood pressure by respiration; and/or
- noise in the optical and pressure signals.

Further, it is preferable to find DBP and SBP automatically.

In order to obtain DBP and SDP automatically, the processor of the PHHM of WO 2014/125431, WO 2014/125431 and of the present invention may be adapted to represent the stress/strain law of the artery wall by a power law when the TMP is positive and zero when it is negative. The power k is of the order of 0.25 to 0.4. It may also be adapted to represent a decay law of pressure field with a parametric function. This parametric function may be exponential.

The optical intensity, i.e. the intensity of the light through the tissue, is represented by a decay law such as an exponential decay, falling exponentially with distance, with a coefficient $\alpha$ per mm, where $\alpha$ is of the order of 0.1 to 0.2. The pressure created by the interaction of the blood flow occlusion means and the body part of the subject is represented by a decay law such as an exponential decay, falling exponentially with distance from the edge of the blood flow occlusion means, with a coefficient b per mm, where b is of the order of 0.1 to 0.3. The pressure signals at the times of each of the maximum and minimum of the optical signal, corresponding to the maximum and minimum pressure in the artery, take account of the push-back by the artery when it expands.

The processor may be further adapted to integrate a plurality of contributions along an artery within the body part of the subject to calculate a total optical signal. The total optical signal may be found by integrating the incremental contributions along the length of the artery, from the centre of the open surface to a point at which the contribution becomes negligible. Each incremental contribution is subject to the decay laws of the intensity of the light and the pressure.

An additional parametric function may be generated by the processor to represent the effect of respiration on blood pressure. The respiration cycle may be estimated from the timing of the pulse and the amplitude of the ECG signal. This is described in WO 2014/125431, page 17, lines 14 to 23. The minimum pressure in the artery, corresponding to DBP, may be largely unaffected and the maximum pressure in the artery, corresponding to SBP, is changed by an amount equal to r times the measured respiration phase, where r typically is in the range of −2 to +2 mmHg if the respiration phase runs from −1 to +1. Optionally r may also be a function of the amplitude of the respiration signal.

The processor may be further adapted to carry out a process to measure the DBP value and the SBP value, wherein the DBP and the SBP values may be estimated in such a way that the difference between the measured optical signals and those that would have been generated by the estimation of the DBP and SBP values is minimized. The processor may use a genetic algorithm to estimate the DBP and SBP values.

The process of measurement of DBP and SBP values may further comprise calculating initial DBP and SBP values without taking account of respiration and re-calculating the DBP and SBP values based on an estimate of respiration and the initial DBP and the SBP values.

The processor may be further adapted to calculate an error estimate, wherein this error estimate is used to weight particular segments of data used for the measurement of the DBP and SBP values.

The processor may be further adapted to obtain an estimate of the value of a parametric function which describes the stress/strain law of an artery wall, wherein this value indicates arterial health and/or age of the subject. The stress/strain law of the artery wall may be represented by a power law when the TMP is positive and zero when it is negative. The power k is of the order of 0.25 to 0.4. The optical intensity may be then calculated by the processing means as a function of k, a, b, r, DBP and SBP and the measured pressures. The analytical process may be the following:

- assuming values for each of the variables k, a, b, r, DBP and SBP;
- calculating the optical intensity signal that they would give;
- calculating the error estimate (the error estimate may be the difference between the calculated optical signal and the measured optical signal); and
- searching through values of k, a, b, r, DBP and SBP to minimize the sum of the errors across all beats.

Searching through values of k, a, b, r, DBP and SBP to minimize the sum of the errors across all beats can be conducted using the so-called genetic approach to improve speed and convergence. It can also be broken into sequential stages by finding an approximate value for the variables that have the greater impact on the errors and then searching around that value for the other variables. Both the red and infra-red optical signals may be included in the search. The error estimate calculation may be weighted to minimize the impact of noise, especially the occasional wild point, and to apply greater significance to the data points that contribute most to the accuracy of the estimates of DBP and SBP.

By this means, DBP and SBP are found analytically with few arbitrary assumptions. The optimal values of k, a, b, r also have value as they are related to the health of the subject and may also be used to identify the subject. For example, k is a measure of the flexibility of the artery and generally increases with age. a, b and r all vary between individuals and may be used in an algorithm to verify the identity of the subject.

The obtained decay law of the optical intensity, the pressure field and the value of the parametric function which describes the stress/strain law of an artery wall may be used by the processor of the PHHM to verify the identity of the subject. It may be possible to calculate a relationship of the measured SBP value and the subject's respiration as an indicator of the subject's respiratory and/or cardiac health and/or the identity of the subject.

Fifth Aspect of the Invention—An Alternative Approach

The analysis disclosed in WO2014/125431 and above is based on measuring the change in PPG signal between diastole and systole. This is analogous to the approach adopted for conventional automated sphygmomanometers but using the PPG rather than the pressure signal. The approach described above uses the PPG and the pressure signals within a mathematical model to find SBP and DBP. This approach is effective but requires data to be collected at a wide enough range of pressures to find the difference between the predicted and measured curves. Typically 30 to 50 pulses are needed to make an accurate measurement, which can take up to 1 minute. There would be advantages for the subject if this could be reduced.

According to a fifth aspect of the present invention, there is provided a PHHM for the measurement of a subject's BP and, optionally, one or more other vital signs, comprising a housing located on a PHHCD or a hand-held component of a computing system; a blood flow occlusion means located in the housing such that an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHM is adapted to process electrical signals acquired by the PHHM to provide at least a measurement of the BP of a subject by measuring a DBP value and a SBP value, wherein the DBP and the SBP values are found by examining the absolute value of a PPG signal at diastole and systole, respectively, as a function of the measured external pressure. Such a PHHM enables a reduction in the time required for an accurate measurement.

The PHHM may be a PHHM as described in either of WO2013/001265 and WO2014/125431 or a PHHM comprising a SAD according to the first or second aspect of the present invention.

Preferably, in the above PHHM, the DBP and SBP are found as the intercept of a fitted line of pressures above the DBP or SBP respectively and a fitted line of pressures below the DBP and SBP respectively.

Preferably, in the above PHHM, the processor is adapted to analyse the absolute value of the PPG signal as a function of time in order to mitigate temporal variations in the intensity of light available to be absorbed by the artery.

Preferably, in the above PHHM, the processor is adapted to make an initial estimate of the DBP and SBP, to instruct the user by means of audible or visual instructions to vary the pressure between the PHHM and the body part and to gather further data points with the external pressure close to those estimates so as to refine their accuracy.

Consider first the diastole. If the external pressure is equal to or just greater than DBP, the artery will just collapse at the lowest pressure in the cycle. If the external pressure is slightly lower, the artery will remain expanded.

FIG. 11 shows a plot of the absolute PPG signal at diastole against the measured external pressure. The signal rises when the pressure is above DBP because the artery is collapsed and so its luminal area is reduced and there is less absorption of the light.

The tissue in the body part in contact with the PHHM behaves as if it were viscoelastic. The viscous element of its properties allows it to flow slowly during the course of the measurement. This can change the amount of light transmitted through the artery and so shift the baseline for the measurement of the PPG signal. This effect can be detected and mitigated by modifying the plot of FIG. 11 as shown in FIG. 12, where the absolute PPG signal at diastole is plotted against time, so showing the sequence of measurements. The measurements can be grouped into two classes: those where the external pressure is above DBP (on the dotted line) and those where the pressure is lower. Between these is the value of DBP. The slope of the line reflects the shift in the baseline.

It will be apparent to a person skilled in the art that an equivalent process may be used to find SBP. FIG. 13 shows the corresponding plot. SBP and DBP may be found in either order, but there is some advantage in finding SBP before DBP if the analysis is carried out in real time rather than retrospectively at the end of the data collection.

Use of Pressure Change

Conventional automated sphygmomanometers detect the change in pressure in the cuff on each pulse, which is typically around 1.5 mmHg, which is assumed to be monotonically related to the change in area of the artery when the pressure within the artery goes from DBP to SBP. The measured change in pressure is plotted against the average pressure in the cuff. The resulting curve rises as the pressure in the cuff falls through SBP and falls again as the pressure in the cuff passes through DBP. Empirical rules are used to estimate SBP and DBP from the shape of this curve.

The analysis disclosed in WO2014/125431 and in the two approaches described above use the relationship between measured optical signals and measured pressures to estimate the SBP and DBP of the subject. The pressure measured by the PHHMs of WO2014/125431 and above changes on each pulse due to the increase in area of the artery when the pressure inside it increases at systole. This is analogous to the change of pressure in a conventional cuff. It has been found that SBP and DBP can be determined to greater accuracy if the magnitude of that incremental change in measured pressure is also included in both of the approaches disclosed in further detail above. It has been discovered that this is advantageous because the change in pressure in the pressure sensor is much greater, perhaps by as much as 25 mmHg, than in a conventional automated sphygmomanometer. This inclusion may be conveniently introduced by adding an extra error term to that included in the estimate described above. The extra error term is a measure of the difference between the values of the incremental change in pressure on each pulse that are predicted by the model and those that are measured.

Preferably, the processor of the PHHM of either the fourth or fifth aspects of the invention is adapted to derive other parameters from the measured data.

The quantitative form of the AOPC can be found by fitting the measured values of the optical signal to a parametric representation of the AOPC, such as that proposed by Langeworters et al. (loc. cit.). The parameters of the AOPC may also be informed by an estimate of the arterial stiffness from the Pulse Wave Velocity, derived from the Pulse Wave Transit Time, which in turn is related to the time interval between the peak of the electrical signal and the peak of the optical signal. This technique is described in detail by Padilla J et al., "Pulse Wave Velocity and Digital volume pulse as indirect estimators of BP: pilot study on healthy volunteers" Cardiovasc. Eng. (2009) 9:104-112).

The electrical signals received by the processor may be further analysed to extract an estimate of the pressure waveform throughout the pulse cycle. Preferably, the analysis uses one or both of two independent methods: the pressure deficit method and the pulse timing method.

The pressure deficit method exploits the instantaneous balance between the pressure within the artery and the sum of the pressure applied by the blood flow occlusion means (EAP) and the pressure caused by the tension in the artery wall (TMP). Measured values of the optical signal are used to find the corresponding TMP from the AOPC. The instantaneous arterial pressure is then found by adding the TMP to the measured instantaneous EAP. The curve in FIG. 14 shows the result of such a calculation.

The pulse timing method identifies the times during the pulse cycle at which the optical signal changes from a large signal (small absorption) to a small signal (large absorption) and back, each time being measured with respect to the time of the peak of the electrical signal. The artery opens when the pressure within it exceeds the pressure applied by the blood flow occlusion means and collapses when the pressure falls below it. The pressure applied by the occlusion means at the time of these events allows the instantaneous pressure to be mapped through the pulse cycle.

Preferably, the instantaneous pressure wave derived from either or both of these methods is then used to model the effect of the reflection of the pulse wave from the body part of the subject which, in turn, is used to estimate the pressure at other parts of the body including, but not restricted to, the wrist, upper arm and aorta (see, for example, Stergiopolus et al, "Physical basis of pressure transfer from periphery to aorta: a model-based study" Am. J. Physiol., 1998, 274, H1386-H1392).

Preferably, the models used to analyse the data make use of information provided by the subject such as height, weight, waist circumference, finger diameter and age.

The estimate of blood pressure may be further refined by the use of other measurements. The Pulse Wave Velocity may be used to make a direct independent estimate of blood pressure as described in detail by Padilla (loc. cit.), which in turn references earlier work on a similar subject from 1995 and its specific use for estimating of BP in 2000. The technique is described in U.S. Pat. No. 5,865,755 dated 2 Feb. 1999. Once the form of the AOPC is found, it is possible to compute the instantaneous pressure throughout the pulse cycle. This allows the PHHM to perform the functions of a tonometer. It also permits a rapid estimate to be made of SBP and DBP, within one cycle, so allowing beat-to-beat monitoring of blood pressure.

In a further analysis of the electrical signals, it is well known that respiration modulates the timing of the heartbeat, the amplitude of the ECG signal, the mean and pulse BP and possibly also the Pulse Wave Velocity. The analysis may exploit all of these to make several independent measurements using: the pulse period derived separately from the red and infrared channels of the optical sensor and from the electrical sensor; the phase difference between said optical and electrical signals; the amplitude and mean values of the PPG signal; and the amplitude of the ECG signal. All of these may be subject to noise or inaccuracy. Each may be independently analysed to establish its quality, measured using parameters such as the repeatability of the periodicity and the signal/noise ratio. The independent measurements may be then combined to give a robust estimate of respiration rate and depth by including all measurements where the quality exceeds an empirically determined threshold.

Some or all of the data analysis of the signals concerning blood pressure may be conducted on a remote computer. This allows more demanding calculations to be provided, such as the analysis required to find the AOPC and to enable the PHHM to be used as a tonometer. Communication with a remote computer also permits the results to be archived and, if the subject so instructs, transferred electronically to third parties such as the subject's personal doctor, a medical specialist or a medical or life insurer.

Sixth Aspect of the Invention—Positioning User's Finger

According to a sixth aspect of the present invention, there is provided a PHHM for the measurement of a subject's BP and, optionally, one or more other vital signs, comprising a housing located on a PHHCD or a hand-held component of a computing system; a blood flow occlusion means located in the housing such that an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHCD or computing system is adapted to process signals acquired by the pressure sensor and the blood flow detecting means to provide at least a measurement of the BP of a subject, which further comprises at least one user interface adapted to produce prompts via the user interface for instructing the user so as to improve the measurement of the subject's BP and, optionally one or more other vital signs. The prompts may be for instructing the user to enter data into the PHHM via the user interface and the data are used to improve the measurement of the subject's BP and, optionally, one or more other vital signs. The prompts may be for instructing the user to change the interaction between the blood flow occlusion means and the body part which is in contact with it to improve the measurement of the subject's BP and, optionally, one or more other vital signs.

The PHHM may be a PHHM as described in either of WO2013/001265 and WO2014/125431 or a PHHM comprising a SAD according to the first or second aspect of the present invention.

One feature of such interaction concerns the positioning of the body part, such as a finger. Preferably, the processor of the PHHM is adapted to detect the position of the finger, to instruct the user to change it, and to correct any errors caused by misposition.

Preferably, the activities associated with artery location are carried out during the initial phase of a two-phase measurement cycle. In the initial phase, the processor of the PHHM makes measurements to locate the artery and/or other measurements that ensure that the subsequent phase will be accurate and efficient, such as approximately determining SBP and DBP. In the second phase, the processor of the PHHM makes the accurate measurements.

In one alternative, the PHHM comprises one or more cameras and the PHHM is adapted to: obtain one or more images of the body part of the subject in contact with the blood flow occlusion means; process the one or more images of the body part of the subject to analyze the relative locations of the body part of the subject and the blood flow occlusion means; and provide visual and/or audible signals based at least on the processing of the one or more images, wherein the visual and/or audible signals provide the user with guidance to optimize the relative locations of the body part of the subject and the blood flow occlusion means.

In a second alternative, the PHHM is adapted to analyze the signals transmitted from the pressure sensor and/or the photodetector and provide visual and/or audible signals based additionally on the signals transmitted from the pressure sensor and/or the photodetector.

The data in FIG. 13 provides further information that may be used to correct for errors in the position of the body part.

The signal shown in FIG. 13 can be thought of as the sum of two parts:
1. the signal due to absorption of light by the section of the artery that is pressed on the blood flow occlusion means; and
2. the signal due to the light from the at least one infra-red and visible LEDs that has travelled through the tissue to regions outside the blood flow occlusion means, so being scattered from parts of the artery that are not subjected to the same pressure as the regions of the artery that are over the blood flow occlusion means, as described in further detail above.

This is represented in FIG. 15. Line 1501 shows the contribution due to part 1, with a sharp discontinuity at SBP. Line 1502 shows the contribution due to part 2, with no discontinuity at SBP. Line 1503 shows the sum of these, with a discontinuity at SBP that is less sharp.

In practice, it is more complicated. If the finger is rotated with respect to the blood flow occlusion means about the finger's long axis, the artery will not be placed centrally over the blood flow occlusion means. The pressure at the artery will be lower than that at the surface of the blood flow occlusion means. The consequence is that the left section of line 1501 of FIG. 15 would be modified as the dotted line 1504. The slope is reduced because the pressure scale is effectively stretched and the intercept with the right section of line 1501 is displaced to higher pressure because the intercept occurs when the pressure at the artery is equal to SBP. As a consequence, the left section of line 1503 is also modified as the dotted line 1505. The intercept with the right section of line 1503 is also displaced to higher pressure.

Similar arguments operate at DBP but the slope of line 1502 is smaller so the effect is less easy to detect.

The gradient of line 1505 at SBP can be used to estimate the displacement of the artery with respect to the gel and the displacement of the estimated SBP.

A third independent estimate of the rotation of the finger may be obtained from analysing the relative amplitudes of the pressure fluctuations and the PPG signals. The pressure fluctuations are the change in pressure between diastole and systole, as used in the oscillometric method of measuring blood pressure, and are caused by the expansion of the artery causing the pressure to increase within the tissue. The PPG signals are the difference in PPG between diastole and systole. If the finger is rotated so that the artery is not over the blood flow occlusion means, the pressure fluctuations are strongly attenuated and can even become negative. The PPG signals are only weakly attenuated because the light travels easily through the tissue.

The ratio of pressure fluctuation to PPG is an indicator of the rotation of the finger. Preferably it is averaged over several pulses and weighted to give more significance to the larger pulses because the data from these is less noisy. An indicator that has been found to be effective is:

$$\text{ratio} = \text{average}\ \{(\text{pressure fluctuation}) \times \text{PPG}/(\text{peak PPG})\}$$

where:
the average is taken over several pulses;
pressure fluctuation=(pressure at systole—pressure at diastole) for each pulse;
PPG=PPG at diastole—PPG at systole; and
PPG peak=the largest value of PPG of the set of pulses, or the average of the three largest values if there are sufficient pulses.

It will be apparent to a person skilled in the art that other definitions may be used to achieve a similar measure of the relative amplitude of the pressure fluctuations and PPG. The ratio may be used to estimate the displacement of the artery with respect to the blood flow occlusion means.

These three estimates of the displacement of the artery with respect to the blood flow occlusion means may be used independently or combined to give an improved estimate of the displacement to detect and, for small rotations, correct the resulting errors in SBP and DBP:
if the displacement is small and thus the slope of line 1505 is not very different from its normal value for a correctly placed finger and/or the ratio is not very different from its ideal value, the difference between the false SBP and the true SBP can be calculated by simple geometry;
the pressure scale may be assumed to have been stretched linearly so a proportionate correction may also be found for DBP; and
if the error is large and thus either the slope of line 1505 is very different from its normal value for a correctly placed finger or there is no clear discontinuity between the left and right sections of line 1503, the measurement may be rejected and the user invited to reposition the finger.

In a third alternative, the PHHM is adapted to estimate the shear force between the body part of the subject and the blood flow occlusion means and the estimation of the shear force is used at least to increase the accuracy of estimation of the subject's BP and/or temperature. The PHHM may be further adapted to provide feedback to the user based on the estimation of the shear force, where said feedback is used to reduce the magnitude of the shear force. The shear force may be estimated based on signals provided by a plurality of pressure sensing elements in the blood flow occlusion means. Preferably, the plurality of pressure sensing elements are adapted to estimate the displacement of an artery within the body part of the subject in contact with the blood flow occlusion means. The estimation of the displacement may be calculated based on the amplitude of a pressure pulse detected by the plurality of pressure sensing elements when the artery expands during said pressure pulse and the estimation of the displacement is used at least to increase the accuracy of estimation of the value of the subject's BP.

Alternatively, the magnitude of the pressure gradient across a MEMS may be used by the processor in order to estimate the shear force between the body part of the subject and the blood flow occlusion means. The change in the magnitude of the pressure gradient across the MEMS when the heart beats (i.e. on systole) may be calculated in order to estimate displacement of an artery within the body part of the subject in contact with the blood flow occlusion means.

Preferably, for any of the alternatives referred to above, the PHHM is adapted to generate a correction factor based on the relative locations of the body part of the subject and the blood flow occlusion means, wherein said correction factor is used to increase the accuracy of estimation of the value of BP. The PHHM may also be adapted to provide feedback to the user based on the estimation of the displacement of the artery, wherein said feedback is used to improve the position of the body part of the subject.

Seventh Aspect of the Invention—Display of Guidance Signal

WO2013/001265 and WO2014/125431 disclose the use of audible or visual instructions to guide the user to adjust the pressure between the body part and the blood flow occlusion means. Such instructions are in part determined by the difference between the instantaneous measured pressure and a target pressure defined by the processor. A difficulty with this is that the instantaneous pressure changes greatly on each systole, by up to 25 mmHg. It is difficult to judge how hard to press when the measurement changes by this amount. This aspect of the invention provides a PHHM which aims to reduce this effect.

This seventh aspect of the invention provides a PHHM for the measurement of a subject's BP and, optionally, one or more other vital signs, comprising a housing located on a PHHCD or a hand-held component of a computing system; a blood flow occlusion means located in the housing such that an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHCD or computing system is adapted to process signals acquired by the pressure sensor and the blood flow detecting means to provide at least a measurement of the BP of a subject, wherein the processor is further adapted to:

provide audible or visual instructions to the user to adjust the pressure between the blood flow occlusion means and the body part in response to signals from the PHHM so as to ensure that measurements are made at a sufficient range of applied pressures to allow the estimation of SBP and DBP, and correct the signal used to provide the audible or visual instructions by a term proportional to the instantaneous value of the difference between the PPG signal and its value at the preceding diastole, the constant of proportionality being adjusted to minimise residual fluctuations of the signal used to provide the audible or visual instructions.

The signal used to indicate to the user how hard the user is pressing (the "guidance signal") is made up of the sum of the instantaneous measured pressure and a term linearly related to the instantaneous value of the PPG signal. The relationship is continuously adjusted to minimise the resulting fluctuation of the guidance signal.

It is found that there is advantage in also using an audible interaction. This can take one of two forms:

for the way of estimating blood pressure disclosed above, a recording of the sound associated with a heartbeat each time the processor detects a pulse. This is particularly helpful for an non-professional user who is reassured by the familiar sound that the device is working correctly; or for the way of estimating blood pressure disclosed above, a recording of the appropriate Korotkov sound according to whether the user is measuring diastolic or systolic blood pressure and whether the measured pressure is above or below the relevant blood pressure. This is particularly helpful for medical professionals who are familiar with the sounds from the use of a stethoscope during conventional auscultation.

Preferably, the display of the measured blood pressure addresses the intrinsic limitations on the repeatability of measurements of blood pressure. Successive measurements may differ by of the order of 5 to 10 mmHg and the measured systolic and diastolic blood pressures may vary by of the order of 20 to 50 mmHg in the course of the day. This is understood by medical professionals but can be worrying for non-professionals. There are internationally recognised guidelines as to the clinical significance of the levels of SBP and DBP. Two ways of presenting the results using those guidelines have been found to reduce their concern:

displaying the instantaneous (i.e. latest) result in small figures and a rolling average of the last few measurements in larger figures (see FIG. 16); or displaying the result graphically with a large or alternatively diffuse symbol (see FIG. 17).

The PHHM may be a PHHM as described in either of WO2013/001265 and WO2014/125431 or a PHHM comprising a SAD according to the first or second aspect of the present invention.

Eighth Aspect of the Invention—Electrical Signals

According to the eighth aspect of the present invention, there is provided a PHHM for the measurement of a subject's BP and, optionally, one or more other vital signs, comprising a housing located on a PHHCD or a hand-held component of a computing system; a blood flow occlusion means located in the housing such that an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHCD or computing system is adapted to process signals acquired by the pressure sensor and the blood flow detecting means to provide at least a measurement of the BP of a subject and wherein there is a first electrode associated with the blood flow occlusion means and the PHHCD or the hand-held component of the computing system includes a second electrode, electrically isolated from the first electrode, against which a part of the body of the subject can be pressed.

The two electrodes may be contacted by at least one finger from each hand of the subject. Preferably, one of the electrodes of the electrical sensor is associated with the open surface of the blood flow occlusion means. The other electrode will be located on a separate part of the PHHM, e.g. on the PHHCD or the hand-held component of the computing system.

Preferably, the signal which is acquired by the electrical sensor provides a measure of the potential difference between the two electrodes which can be related to the potential difference between the two different body parts of the subject.

The two electrodes can be used to detect electrical signal between two parts of the body and hence provide an ECG. In one preferred embodiment, the PHHCD is a cellphone, one electrode is part of the housing on which the user places a part of the body, such as the index finger of one hand, and the other electrode is located on the side of the cellphone where it can be contacted by another part of the body, such as the index finger of the other hand.

There is benefit in maximising the areas of contact to obtain the best signals. Many cellphones have a band of metal or metallised plastic around their perimeter, as shown in FIG. 18A in which there is shown a cellphone with a screen 1801 and a band 1802. A preferred design shown in FIG. 18B introduces an insulating break 1803 that splits that band into two electrically-isolated regions, each of which is in contact with a respective hand, and connects the two regions as the two electrodes of the PHHM. Not shown is a similar insulating break on the opposite side of the cellphone to 1803.

The PHHM may be a PHHM as described in either of WO2013/001265 and WO2014/125431 or a PHHM comprising a SAD according to the first or second aspect of the present invention.

Ninth Aspect of the Invention—Temperature Effects

The SADs of the present invention and the PHHMs of WO2013/001265 and WO2014/125431 use electronic sensors to measure pressure, voltage, light and other signals. The signals from such sensors can be affected by temperature as well as the property that they are intended to measure. Preferably, each sensor is calibrated at various temperatures and the calibration parameters are stored in the PHHCD or computer system of the PHHM. They are then used to remove the effects of temperature and obtain an estimate of the property of interest.

During a measurement, the temperature of the SAD, the PHHCD or the hand-held component may change by several degrees due to heating by the body part with which it is in contact. Some of the electrical components within the SAD, the PHHCD or the component dissipate heat so the temperature may not be constant throughout the PHHM. A large and non-uniform temperature change can give rise to effects that are not adequately represented in the calibration chamber, so are not perfectly removed by the calculations carried out by the PHHCD or the computer system. The result is that the value of the property being measured, such as pressure, is not the same when the PHHM is removed from the body part as it was before touching. This difference is measured and used to adjust the calibration parameters to reduce it, ideally to zero. This adjustment may be derived from a tracking filter so as to reduce the errors due to a single erroneous measurement.

Tenth Aspect of the Invention—Use of Games

According to a tenth aspect, the present invention provides a PHHM for the measurement of a subject's BP and, optionally, one or more other vital signs, comprising a housing located on a PHHCD or a hand-held component of a computing system; a blood flow occlusion means located in the housing such that an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHCD or computing system is adapted to process signals acquired by the pressure sensor and the blood flow detecting means to provide at least a measurement of the BP of a subject and wherein: the PHHM has at least one user interface; the PHHM is adapted to produce prompts via the user interface for instructing the user so as to improve the measurement of the subject's BP and, optionally, one or more other vital signs; the at least one user interface displays a videogame and the prompts are to instruct the user to implement videogame actions; and the videogame is adapted to mitigate the impact on the measured vital sign of the psychological and/or physiological effects of making the measurement.

Preferably, the PHHM stores a plurality of user-selectable, different videogames for display on the user interface. The PHHM may also be adapted to download and install additional videogames for display on the user interface.

It is commonly known that the process of measuring some vital signs may itself cause a change in the measured values. This is known as the "white coat syndrome" and often occurs when measuring blood pressure. Similar effects may be seen when measuring respiration rate. As disclosed above, the use of games can facilitate the operation of the PHHM by the subject. The use of such games may make the PHHM easier to use and may encourage the subjects to make frequent checks of their vital signs. An interface that resembles a game can prove distracting for the subject so as to avoid the occurrence of "white coat syndrome".

The PHHM may be a PHHM as described in either of WO2013/001265 and WO2014/125431 or a PHHM comprising a SAD according to the first or second aspect of the present invention.

Eleventh Aspect of the Invention—Identification of User

WO2013/001265 (page 15, lines 6 to 14) discloses the use of an additional sensor for identification. WO2014/125431 (page 11, lines 16 to 19) discloses a refinement of this in which the additional sensor is located so as to ensure that the identity of the subject may be confirmed when taking a measurement of a vital sign.

As an alternative to this, which is an eleventh aspect of the present invention, there is provided a PHHM for the measurement of a subject's BP and, optionally, one or more other vital signs, comprising a housing located on a PHHCD or a hand-held component of a computing system; a blood flow occlusion means located in the housing such that an open surface of the blood flow occlusion means is available to be pressed against a body part of the subject or to have a body part of the subject pressed against it; a pressure sensor adapted to provide an electrical signal indicative of the pressure applied to or by the open surface; a means for detecting the flow of blood in the body part of the subject when pressure is applied to or by the open surface; and means for receiving electrical signals from the pressure sensor and the blood flow detecting means and for transmitting electrical signals indicative of the pressure and blood flow to the processor of the PHHCD or the computing system, wherein the processor of the PHHCD or computing system is adapted to process signals acquired by the pressure sensor and the blood flow detecting means to provide at least a measurement of the BP of a subject and wherein the processor of the PHHM is adapted to use at least one of the measurements used to derive at least one of the parameters related to the health of the subject to identify the subject.

For instance, for this purpose, the processor of the PHHM may use the decay law of the optical intensity or the pressure field or the value of the parametric function which describes the stress/strain law of an artery wall to verify the identity of the subject.

The PHHM may be a PHHM as described in either of WO2013/001265 and WO2014/125431 or a PHHM comprising a SAD according to the first or second aspect of the present invention.

The behaviour of the artery wall under stress/strain and the behaviour of optical intensity and the pressure field under the decay laws are examples of such an identifier and may also be correlated with specific subject characteristics such as age.

The present invention also provides a PHHM as referred to above, wherein the processor is adapted to extract one or more features from the signals acquired by the PHHM that is(are) correlated with the identity of the subject.

Preferably, in the above PHHM, the signals are one or more of the optical, pressure and electrical signals or signals derived from them.

Preferably, in the above PHHM, the features are Pulse Wave Transit Time (the interval between the QRS complex in the ECG signal and the arrival of the pressure pulse in the optical signal); the timing and amplitude of the dicrotic notch in the optical and pressure signals; the width of the pressure and optical pulses; pulse rate; pulse rate irregularity; or the shape of the QRS complex in the ECG signal or any combination of two or more of these.

Preferably, in the above PHHM, the feature is the area of the pressure and/or optical pulses.

Preferably, in the above PHHM, the processor is adapted to combine the individual features using Bayes theorem to make an optimal estimate of the probability that information has been obtained from a known individual whose characteristics have been previously described.

Preferably, in the above PHHM, the level of probability that is required to verify the identity of the individual is adjusted according to the harm caused by either a false positive or false negative match.

Preferably, in the above PHHM, the probability or the values of the extracted features is/are communicated to another computing device by means of a wireless link or a cable.

As shown above, it has been discovered that other indicators of identity can be used and a systematic way of combining them to give an optimal estimate has been developed. There are many features of the data measured by the PHHM when estimating the vital signs that can also contribute to an identification or at least verification of the subject's claimed identity.

FIG. 19 shows data recorded from a prototype PHHM. There are four traces, being (top down) the Red PPG, the IR PPG, the ECG and the pressure signal. Four complete heartbeats are shown. The data is noisy, particularly for the ECG which can occur if the user holds the PHHM awkwardly or has unusually dry skin.

The features that are marked in FIG. 19 are:

1901—Pulse Wave Transit Time (the interval between the QRS complex in the ECG signal and the arrival of the pressure pulse in the optical signal);

1902—the amplitude of the dicrotic notch in the IR signal;

1903—the timing of the dicrotic notch in the IR signal;

1904—the rate of change of the QRS complex in the ECG signal; and

1905—the pulse interval.

It is clear that others may be found, such as the dicrotic notch data for the optical and pressure signals, the area of the pressure and optical pulses and the variability of the pulse interval, as well as those previously disclosed. The PHHM of this aspect of the invention has the great advantage over competing solutions in that it measures all of the data simultaneously, so allowing the derivation of data that depends on combinations of signals.

Some of the features of the data would be, by themselves, poor measures of identity. This could be because they are noisy, in the sense that the uncertainty of their measurement is not small when compared with the differences between individuals. They might also be variable; for example, a subject's pulse rate can vary significantly with circumstances. A preferred feature of this aspect of the present invention is to combine the separate features optimally using a Bayesian estimator. It is only necessary that there is some correlation between a feature and the subject for that feature to be used to increase or reduce the probability that he or she is a particular person. For an identification system, the aim is to answer a question in the form "What is the probability that this person is X, given that he claims to be X, that X has PPG characteristics a, b and c and this person has PPG characteristics d, e and f, and X has ECG characteristics p and q and this person has ECG characteristics r and s?". This can be posed in terms of a sequence of conditional probabilities that are combined according to the rules of Bayes theorem to create an overall degree of confidence.

A Bayesian formalism allows other parameters to be incorporated if they are correlated with identity. Such parameters might include the degree of vibration of the PHHCD (derived from its internal sensors) or facial characteristics (derived from images obtained by a front-facing camera in the PHHCD).

The robustness may be adjusted to suit the context so that, for example, a claimed identity might need to have a higher probability of being correct to allow access to a bank account than to a less sensitive service.

Twelfth Aspect of the Invention—Calibration of Optical Sensor

The SAD of either of the first two aspects of the present invention may be designed to be a component of a PHHCD or a hand-held component of a computing system, as referred to above. These devices are sold in very large quantities, typically 1,000 million per year. It is well known that the costs of testing and calibration of mass produced devices can be a large fraction of their total cost. Hence, a way of making the testing and calibration of the SAD fast and inexpensive is desired.

The production tolerances of the components used in the SAD are such that certain of its functions must be calibrated for each device.

The separation of the SAD from the processor makes it more easy to conduct automated testing and calibration of the SAD.

According to a twelfth aspect of the invention, there is provided a holder for transferring a SAD of the first aspect of the invention or the preferred SAD of the second aspect of the invention which comprises a flexible and essentially incompressible gel into a test and calibration facility, the holder comprising: a vacuum pipe adapted to hold the SAD;

and a spring-loaded probe for contacting the flexible and essentially incompressible gel and measuring the height of the flexible and essentially incompressible gel with respect to the open surface.

The holder may further comprise, in one alternative, at least a first photo-detector sensitive to visible light and a second photo-detector sensitive to infra-red light for detecting the light emitted by any LED in response to test signals, in order to test the correct operation of the device under test.

The holder may comprise, in a second alternative, an optical sensing module comprising:
- a fibre-optic cable from the holder to a remote instrumentation box;
- two LEDs of known wavelength (one red, one infra-red) contained within the remote instrumentation box;
- four photo-detectors in the remote instrumentation box, each of which is covered by an optical filter, two of which are used to analyse the red LED under test and the other two of which are used to analyse the infra-red LED under test;
- an optical diffuser within the holder; and
- a processor to control the two LEDs of known wavelength and the two LEDs of the SAD, and to analyse the data measured by the four photo-detectors.

FIG. 20 shows the configuration of these elements. The LEDs under test emit light into the curved area of the device under test 2001, which is held in the holder 2003. The fibre-optic cable 2004 is split into 6 parallel bunches 2005. Four of these bunches transfer light from the inside of the holder to the four optical filters 2007 that cover the four photo-detectors 2006 and two transfer light from the two LEDs of known wavelength 2008 to the holder. The optical diffuser 2002 ensures that the light from all four LEDs illuminates the four photo-detectors in constant ratios. The four photo-detectors and two LEDs of known wavelength are connected to the processor 2009.

FIG. 21 shows the typical spectral response of an inexpensive red LED and FIG. 22 similarly for the two filters used to analyse it. In FIG. 22, the solid curve is the transmission as a function of wavelength of one filter and the dashed curve is the transmission as a function of wavelength of the other filter. FIG. 23 shows the relative value of the signals from the two photo-detectors as a function of the central emission wavelength under test. Two different models are shown. Model 1 is found by calculating (Signal 1−Signal 2)/(Signal 1+Signal 2) and is effective if the central emission wavelength remains close to nominal. Model 2 is found by calculating—Signal 1/Signal 2 if Signal 1 is greater than Signal 2 and Signal 2/Signal 1 if Signal 1 is less than Signal 2. Model 2 is effective when the central emission wavelength is far from nominal. In practice, both are used to estimate the central emission wavelength. It will be obvious to a person skilled in the art that other such models could be used.

The LEDs of known wavelength are used to calibrate the system by measuring the ratio of the signals when they alone are illuminated.

The holder for transferring a SAD may further comprise one or more spring-loaded connectors for making electrical connections to any electrode in order to test its correct operation. The holder may be adapted automatically to release the SAD on demand.

Thirteenth Aspect of the Invention—Socket

According to an thirteenth aspect of the present invention, there is provided a socket that is adapted to hold a SAD as described in either of the first two aspects and connect said SAD into a calibration board, the socket comprising: a plurality of spring-loaded connecting pins; at least two mechanical retaining clips; and a socket well that is adapted to locate the SAD, wherein the socket is adapted to provide electrical connection between the SAD and an external computer.

The socket may further comprise a cut-out provided on the side of the socket well for accommodating a flexible cable for attachment to the SAD.

Fourteenth Aspect of the Present Invention—Calibration of Pressure and Temperature Sensors According to a fourteenth aspect of the present invention, there is provided a method for calibrating a SAD as described in either of the first two aspects, comprising: in a first calibration step, exposing the SAD to different atmospheric pressures and temperatures and measuring the electrical signals generated by the SAD exposed to said different pressures and temperatures after the device has come to equilibrium; and in a second calibration step measuring a bolometric signal based on the exposure of the SAD to a reference source of a black body radiation of a known temperature.

The first calibration may be conducted in a test chamber which is adapted to operate at two different temperatures and three different pressures. The different temperatures may be controlled by a water-filled radiator through which fans force air for circulation around the test chamber. A controller may be adapted to adjust the temperature of the water in the water-filled radiator to maintain a desired temperature at the calibration board. Alternatively the test chamber may have a water jacket, the temperature of which may be similarly controlled.

The SAD may be placed in one of a plurality of sockets, such as those of the thirteenth aspect, of a calibration board, wherein the calibration board is adapted to be inserted into the test chamber and connected to an external computer. Others of the plurality of sockets of the calibration board may contain reference devices by which the different temperatures and/or pressures may be monitored.

The test chamber may be insulated and placed inside a second insulated chamber.

The test chamber may comprise a plurality of calibration boards, wherein each calibration board is equipped with a plurality of sockets into each of which a SAD to be calibrated can be inserted.

The reference source of black body radiation may comprise a plurality of windows aligned with the plurality of sockets to minimize the loss of radiation from said reference source of black body radiation.

In preferred aspects, the SADs and PHHMs disclosed above uses a gel or other fluid-based mechanism to transmit pressure from the body part to the pressure sensing element. This is an effective mechanism that can readily be manufactured at low cost and with high reliability. The indicated pressure is affected by temperature, both because of the differential thermal expansion between the gel and the housing and because of distortions of the housing causing strain in the gel. As disclosed above, the thermal effect may be measured when the device is manufactured and downloaded to the processor as a calibration coefficient, herein called the Coefficient of Temperature Offset (CTO).

It is well-known that the temperature of a MEMS pressure sensing element may be estimated by measuring the resistance between two opposite terminals of the bridge. In the simple case, this is easily implemented by driving the bridge with a constant current and measuring the voltage between the driven and ground terminals, where the pressure is proportional to the voltage between the other two terminals.

A more general solution is set out below. The temperature found from the MEMS pressure sensing element is the temperature of the gel and may be multiplied by the CTO to find the correction that must be added to the indicated pressure to remove the effect of temperature.

This approach is effective but has two limitations: the CTO may change with time as the gel ages; and it assumes that the change in indicated pressure is proportional to instantaneous temperature with no dependence on the temporal sequence of temperatures.

Both of these limitations may be countered by inducing a change in temperature and measuring the effect on the indicated pressure. The two LEDs of the optical sensor dissipate significant power when in use and cause heating. A self-test may be conducted by recording the indicated pressure when the LEDs are turned on or off. The resulting temperature pattern may be fitted to a parametric model of the temperature response to find the coefficients that should be used to correct the indicated pressure.

In one embodiment, it is found that the response of turning on the LEDs is a shift of the indicated pressure that is proportional to the LED current and responds with a time constant of a few seconds. After this, the continued heating causes a change in indicated pressure proportional to the error in CTO. FIG. 24 shows typical results.

The indicated pressure is the value that is found after the nominal CTO (i.e. the value from the calibration) has been applied. The indicated pressure is constant until the LEDs are turned on (2401). The indicated pressure then falls with a time constant of typically a few seconds (2402) by an amount of typically a few mmHg (2403). After equilibrium has been reached, the indicated pressure continues to change at a rate indicated by the slope (2404) that is proportional to the error in CTO. Alternatively the indicated pressure may be plotted against temperature.

This self-recalibration may be carried out automatically according to a schedule, automatically in response to evidence that there is a significant error in CTO or in response to a user request. A significant error in CTO may be detected by comparing the indicated pressure before and after a measurement. The temperature of the PHHM will have changed because of the heat dissipated by the LEDs and other electronic components and due to the warming by contact with the body part. If the CTO is not correct, the indicated pressure after the measurement is complete will be different from that before it started.

The second calibration may be conducted by exposing each calibration board to the reference source of the black body radiation. The reference source may be double-walled with water circulating in the space between the walls. A plurality of sensors may be immersed in the water circulating in the space between the walls to measure the water temperature, wherein the data obtained from the plurality of sensors is used by a controller to operate one or more heaters.

Fifteenth Aspect of the Present Invention—Protective Cover

According to a fifteenth aspect of the present invention, there is provided a protective cover for a PHHM which includes an electrically conductive section for location over an electrode so that, when the cover is located on the PHHM, a part of the subject's body may be pressed against the section and electrical signals from that body part of the subject may be transmitted to the electrode.

BRIEF DESCRIPTION OF THE DRAWINGS

The present invention is further described below, by way of non-limiting example only, with reference to the accompanying drawings, in which:

FIG. 1 is a representation of a SAD incorporating a dam;
FIG. 2A is a representation of a saddle shape for the open surface of a SAD;
FIG. 2B is a representation of another saddle shape for the open surface of a SAD;
FIG. 2C is a representation of another saddle shape for the open surface of a SAD;
FIG. 2D is a representation of another saddle shape for the open surface of a SAD;
FIG. 28 shows a cross-section of a fifth embodiment of a SAD;
FIG. 30A shows a PHHM with a SAD;
FIG. 30B shows a cross-section of the PHHM of FIG. 30A;
FIG. 30C shows a perspective view of a hand holding the PHHM of FIG. 30A;
FIG. 31 shows a location of a SAD on a smartphone;
FIG. 32 shows the position of the artery in a finger and a SAD;

FIG. 33A shows an alternative pressure sensor;
FIG. 33B shows an alternative pressure sensor;
FIG. 33C shows an alternative pressure sensor;
FIG. 33D shows an alternative pressure sensor.

In all embodiments described below, unless otherwise stated, the PHHCD can be a cellphone, tablet computer or MP4 player and the hand-held component can be a component, such as a mouse or a remote controller, of a larger computer system such as a laptop, PC or TV.

DETAILED DESCRIPTION OF THE DRAWINGS

Figure 25:
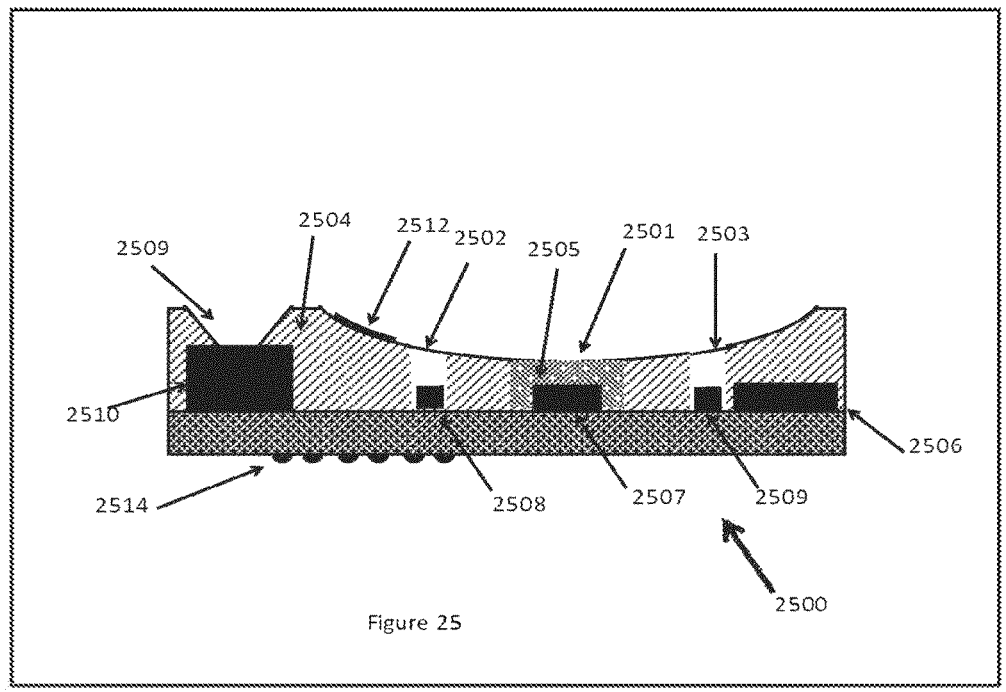
FIG. 25 shows a cross-section of an embodiment of a SAD.

FIG. 25 shows a cross-section of a SAD 2500 as part of a PHHM for measuring BP, intended for use where the body part of the subject is a finger.

The SAD 2500 includes a housing 2504 made of a non-conductive plastic material. The length of the SAD 2500 is approximately 15 mm. The housing 2504 includes a well 2501 in which a flexible and essentially incompressible gel 2505 is located. The housing 2504 comprises electrical connectors 2514 located on the exterior lower surface of the housing 2504 to connect the SAD 2500 to a PHHCD or a hand-held component of a computing system. A pressure sensor 2507 is embedded in the gel 2505. The housing 2504 has embedded infra-red and visible LEDs 2508 and photo-detector 2509. The infra-red and visible LEDs 2508 and photo-detector 2509 access the body part of the subject via windows 2502 and 2503. The SAD 2500 includes a blood flow occlusion means in the form of the open top surface of the housing 2504 against which a finger of the subject can be pressed. The SAD 2500 includes receiving and transmitting means 2506 embedded in the housing 2504. In this particular embodiment, the receiving and transmitting means 2506 includes an ASIC and there is a separate bolometric temperature sensor 2510. Alternatively, the bolometric temperature sensor 2510 could be incorporated as part of the same ASIC 2506. The bolometric temperature sensor 2506 has a window 2509 in the top of the housing 2504 of the SAD 2500.

Preferably, the receiving and transmitting means 2506 is adapted to carry out signal conditioning, such as filtering, analog to digital conversion and amplification. These functions may be carried out by the ASIC, if present. Alternatively, the processor of the PHHM is adapted to carry out the signal conditioning.

The SAD includes one electrode 2512 adapted to be touched by the body part of the subject when it is pressed against the open surface of the housing 2504. Not shown is a further electrode which is adapted to make contact with another body part of the subject.

Figure 26:
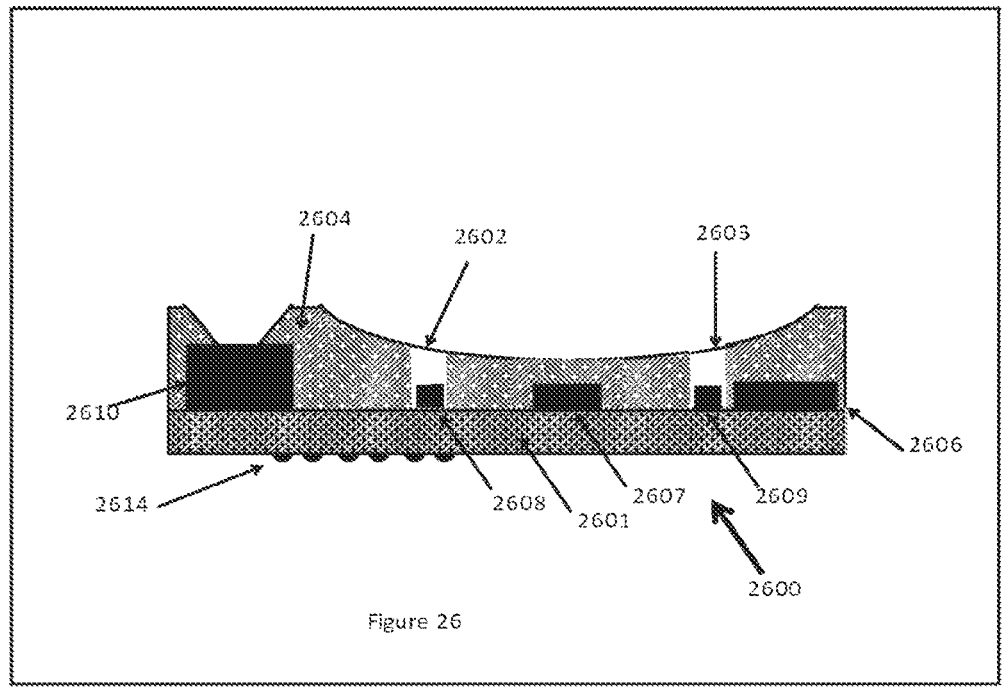
FIG. 26 shows a cross-section of a second embodiment of a SAD

FIG. 26 shows a second SAD 2600. A flexible and essentially incompressible gel 2604 forms the entire housing, without being contained within a well. The open surface is entirely formed by gel 2604. The housing 2604 also comprises electrical connectors 2614 located on the exterior lower surface of its base 2601 to connect the SAD 2600 to a PHHCD or a hand-held component of a larger computing system. The SAD 2600 of FIG. 26 comprises an electrode (not shown) disposed on the open surface of the gel 2604. The electrode is adapted to transmit electrical signals from the body part of the subject pressed against the open surface of the gel 2604 to receiving and transmitting means 2606 via electrical connections (not shown) embedded in the gel 2604. In this particular embodiment, the receiving and transmitting means 2606 is adapted to carry out signal conditioning. The processing routines to obtain the BP of the subject are carried out in the processor of a PHHM. The SAD 2600 of FIG. 26 further comprises a pressure sensor 2607, infra-red and visible LEDs 2608 and photo-detector 2609 and a bolometric temperature sensor 2610 embedded in gel 2604. The infra-red and visible LEDs 2608 and photo-detector 2609 access the body part of the subject via the windows 2602 and 2603.

Figure 27:
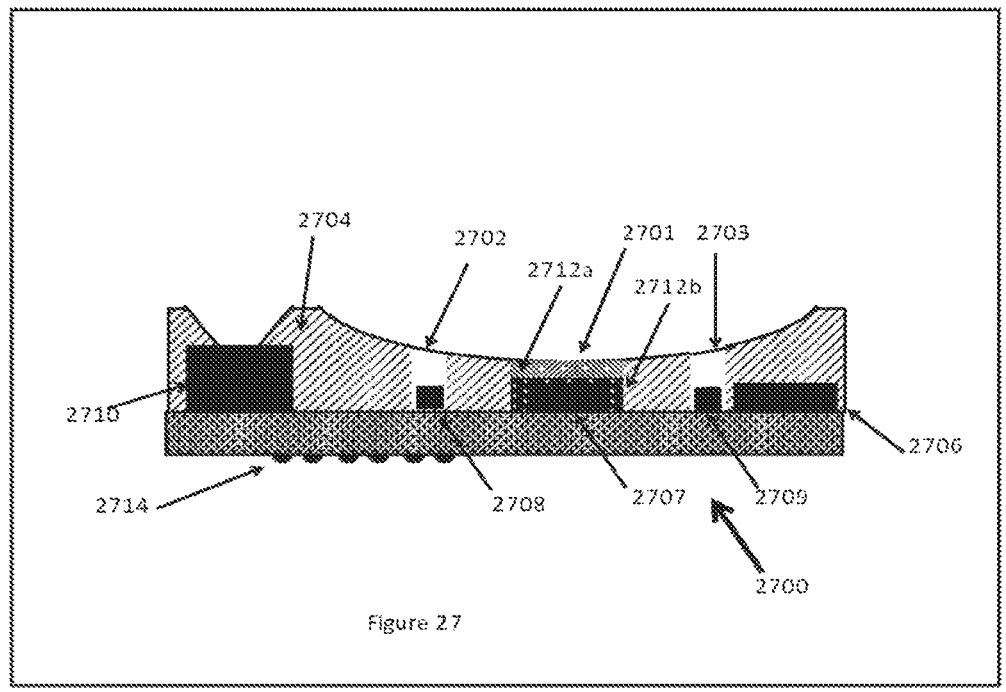
FIG. 27 shows a cross-section of a third embodiment of a SAD.

FIG. 27 shows a SAD 2700 according to a preferred embodiment of the present invention. The SAD of FIG. 27 comprises a housing 2704 which includes a well 2701 in which the flexible and essentially incompressible gel 2712a and 2712b is located. The housing 2704 comprises electrical connectors 2714 located on the exterior lower surface of the housing 2704 to connect the SAD 2700 to the processor of a PHHCD or a computing system. The open surface of the housing 2704 is coplanar with the upper surface of the gel 2712a at the open end of the well 2701. Gel is divided into two layers 2712a and 2712b. The upper layer 2712a is a hard gel, designed to provide a robust surface that will resist physical or chemical damage. Alternatively, the first layer may be a hard material, such as the same material as is used to form the housing. The lower layer 2712b, that extends from the interface between the two layers down to the pressure sensor 2707, is a softer gel which is still essentially incompressible but has low shear strength. An advantage of such a construction is that the shear forces that arise when the open surface is in contact with the body part of the subject are transmitted less well to the pressure sensor 2707. In this preferred embodiment, the receiving and transmitting means 2706 is adapted to carry out signal conditioning. The SAD 2700 of FIG. 27 also comprises an electrode (not shown) disposed on the open surface of the housing 2704. The electrode is adapted to transmit electrical signals from the body part of the subject pressed against the open surface of the housing 2704 to the receiving and transmitting means 2706 via electrical connections (not shown) embedded in the housing 2704. The processing routines to obtain the BP of the subject are carried out in the processor of a PHHCD or a computing system of which the SAD is a part. The SAD 2700 of FIG. 27 further comprises a pressure sensor 2707 embedded in lower layer 2712b, infra-red and visible LEDs 2708 and photo-detector 2709 and a bolometric temperature sensor 2710. The infra-red and visible LEDs 2708 and photo-detector 2709 are also embedded in the housing 2704 and access the body part of the subject via the windows 2702 and 2703.

Figure 28:
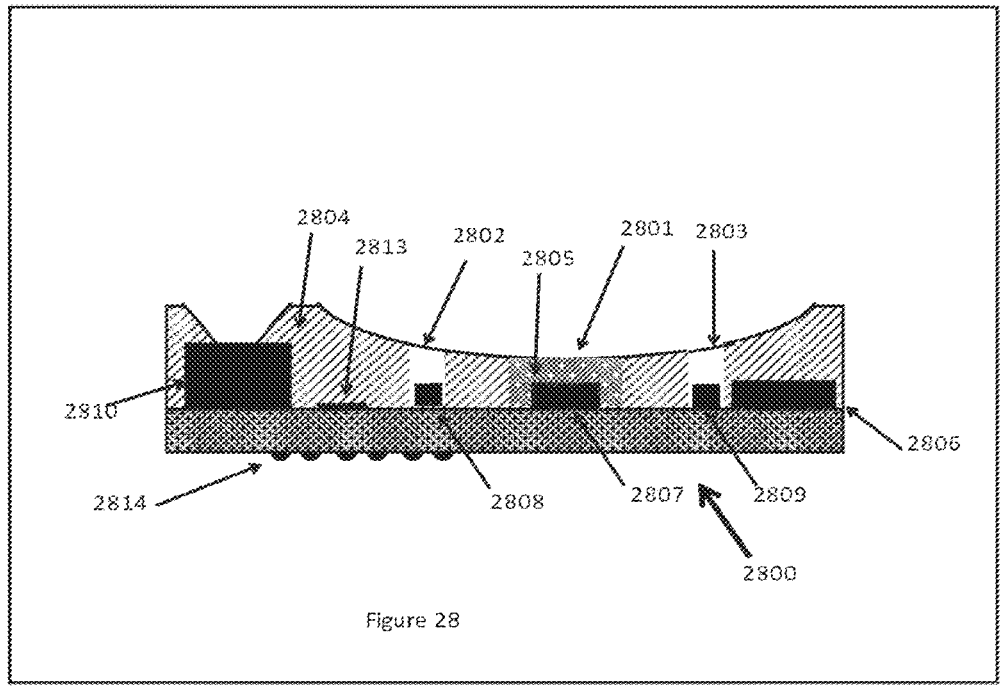
FIG. 28 shows a cross-section of a fourth embodiment of a SAD.

FIG. 28 shows a representation of a SAD 2800 according to a preferred embodiment of the present invention. In this embodiment, the SAD of FIG. 28 comprises a housing 2804 which includes a well 2801 in which a flexible and essentially incompressible gel 2805 is located. The housing 2804 comprises electrical connectors 2814 located on the exterior lower surface of the housing 2804 to connect the SAD 2800 to the processor of a PHHCD or a computing system. The open surface of the gel 2805 is at the open end of the well 2801. In this embodiment, the housing 2804 forming the well 2801 is made of a conductive plastic material. The housing 2804 further comprises one or more electrically conductive pads 2813 in contact with the conductive plastic material. The electrode described with reference to FIGS. 25 to 27 is omitted in this embodiment. The electrical connections (not shown) from receiving and transmitting means 2806 now run to pads 2813 within the housing 2804. The conducting material is chosen so that the resistance between each one of the pads 2813 and the open surface of the housing 2804 is of the order of 50K ohms. This limits the current that would flow through the subject's body part in the event of a fault causing a voltage to be applied to the open surface of the housing 2804. The processing routines to obtain the blood pressure of the subject are carried out in the processor of a PHHCD or computing system integrated with the SAD of FIG. 28. The SAD of FIG. 28 further comprises a pressure sensor 2807 embedded in the gel, infra-red and visible LEDs 2808 and photo-detector 2809 and a bolometric temperature sensor 2810. The infra-red and visible LEDs 2808 and photo-detector 2809 access the body part of the subject via windows 2802 and 2803.

Figure 29:
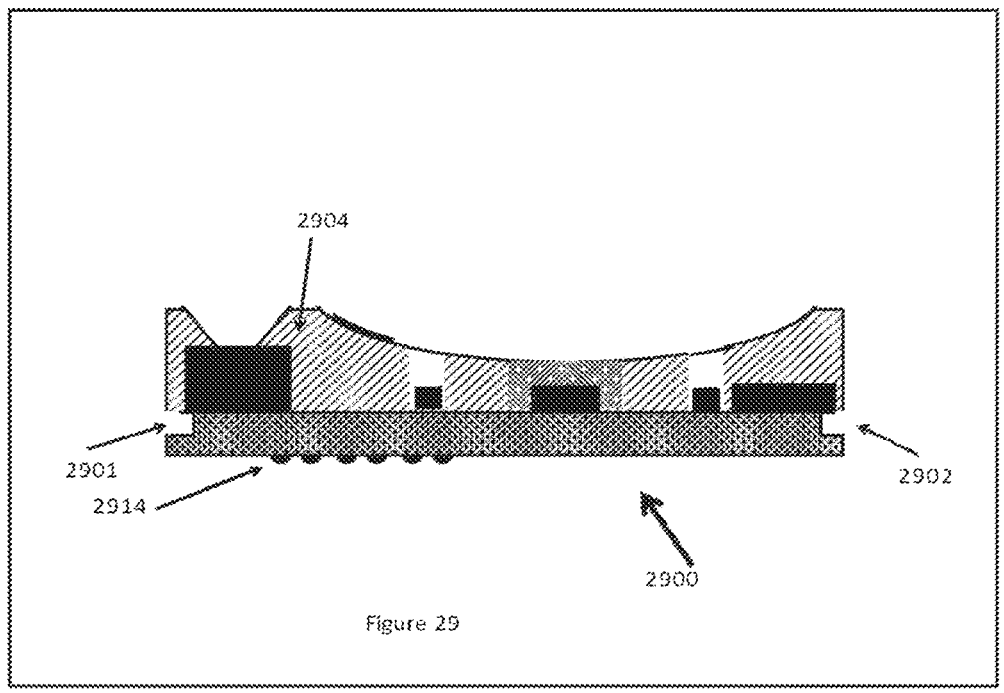
FIG. 29 shows an embodiment of a signal acquisition device.

FIG. 29 shows a SAD 2900 according to an embodiment of the present invention. The SAD 2900 differs from the SAD 2500 of FIG. 25 in that the housing 2904 of the SAD 2900 comprises two cut-outs or slots 2901 and 2902 that allow it to be slid into a mounting guide in the PHHCD or the hand-held component of the computing system. The housing 2904 can conveniently be manufactured by cutting or punching individual devices out of a sheet. The sheet might be manufactured in several layers, with the slots 2901 and 2902 formed by omitting some material from one or more layers. In this case, it is beneficial to restrict the width of the slots to less than the full width of the device so that the layer(s) from which they are removed remains structurally robust. The mounting guide into which the SAD 2900 slides is a component of a PHHCD or hand-held component of a computing system and can include electrical connections that press against electrical connectors 2914 of the SAD. Alternatively, a flexible cable can be soldered to the electrical connectors 2914 and inserted into a socket in the PHHCD or hand-held component of the computing system (not shown).

FIG. 30A shows a PHHM 3000 according to an aspect of the invention. The PHHM 3000 comprises a SAD 3002 and a PHHCD 3001. The SAD 3002 is located on a surface of the PHHCD 3001. During measurement, it can be difficult to position the finger comfortably on the open surface of the SAD 3002 which has a saddle-shape open surface. The saddle-shaped open surface can affect the accuracy of the measurements because the natural reaction when the finger is forced into an uncomfortable position is to tension the muscles. The tense muscles can affect the pressure applied to the artery and can also affect the distribution of tissue between the bone and the skin, which can in turn affect the optical signals.

FIG. 30A shows a modification of the saddle-shape of the open surface wherein the concave section 3003 is not perpendicular to the body of the PHHCD 3001 and the convex section is asymmetric. FIG. 30B shows a plan view of the saddle and a cross-section along the bottom of the concave section.

FIG. 30C is a sketch showing a cellphone as the PHHCD 3001 being held in the right hand of the subject. The SAD 3002 is under the index finger, which falls naturally over the top of the mobile telephone. The concave section 3003 of the SAD 3002 is at an angle of approximately 70 degrees to the longer axis of the surface of the PHHCD 3001.

FIG. 31 shows a preferred embodiment of the present invention which is PHHM 3100. The PHHM 3100 comprises the SAD 3101 according to any of FIGS. 25 to 30 located on a PHHCD or on a hand-held component of a computing system 3102 comprising a user interface 3103. The electrical signals are transmitted from the receiving and transmitting means to a processor of the PHHCD or computing system or vice versa and the PHHM 3100 is adapted to process signals acquired by the SAD to provide at least a measurement of the BP of a subject.

The PHHM 3100 comprises a user interface 3103 which is a display which permits the subject to use the PHHM 3100 as a hand-held games console, used for interactive electronic games. The use of the PHHM 3100 as a hand-held games console provides a convenient way for the subject to operate the PHHM and also allows the results of the measurements of BP and, optionally, one or more other physiological vital signs to be exploited within the game. The steps that are required to operate the PHHM 3100 correctly might cause difficulties for some subjects if they have to read detailed instructions. Many subjects are familiar with playing interactive electronic games and are comfortable using a controller and electronic displays such as on a cellphone or tablet computer. Hence, it is possible to set the measurements made by the PHHM 3100 in a games context so that the subjects are automatically guided to make accurate measurements.

An exemplary game that could be used to derive a measurement of a subject's BP could be a game that represents some of the elements of a biathlon, requiring the player to remain calm when subject to physical or emotional stress. Alternatively, the interface could display two fighter aircraft in the sky. The pressure generated by the subject's finger on the pressure sensor controls the orientation of one of them. The position of the other aircraft is controlled by the pressure that the subject is applying over the SAD of the PHHM based on specific prompts shown to the subject via the user interface. In particular, if a missile is fired from the first aircraft on each pulse and the second aircraft rolls when hit by a missile, then the subject gets immediate feedback that the pressure is correct. This helps the user to adjust the pressure. The data obtained from that point are used even though it was not at the target pressure because it is still a valid data point and adds to the accuracy of the result. Subjects with no knowledge or training would be able to use this video game interface immediately to make accurate measurements of BP.

It is common for devices for monitoring vital signs to be purchased and used a few times but then for the subject to lose interest. An entertaining games interface would encourage the subject to continue monitoring his or her vital signs. Hence, the user interface using a game for some or all of the measurements can automatically guide the subject through the necessary steps and ensure that the device is being used correctly. Information and instructions would be included in the game.

The PHHM may be adapted to store different video games. These videogames could take many forms, such as bat and ball, fighting, shooting, role-play, strategy and pattern-matching such as mazes. The subject may select from a suite of games that are included in the PHHM and new games may be downloaded to the PHHM via the internet.

The PHHCD of the PHHM 3100 of FIG. 31 comprises a frontal camera 3104 and a rear camera (not shown). When the subject uses the index finger as the relevant body part, it is also advantageous to provide guidance to the user to locate the finger correctly with respect to the PHHM. The PHHM 3100 is adapted to interpret the images from the frontal camera 3104 and the rear camera located on the PHHCD. For example, a smartphone typically has two cameras, one facing away from the screen and one facing in the direction of the screen. If the SAD is located on the edge of the smartphone and the index finger is placed on the SAD, the hand and/or finger is in the field of view of both cameras or at least in the field of one of the cameras, typically the rear camera. The images from the cameras provide an indication of its position, and the accuracy of this indication may be further enhanced by relating it to the signals measured simultaneously by the pressure and optical sensor in the PHHM.

The indication of the position of the finger and/or hand so derived may be used by the processor of the PHHCD to generate audible and/or visual feedback to guide the subject to position the finger optimally on the SAD of the PHHM. Alternatively, the indications of position may be used to generate a correction factor to be applied to other measured data to improve the accuracy of the parameter related to health that is being measured.

FIG. 32 shows a representation of the key elements of a preferred embodiment which has a SAD 3203 according to any one of FIGS. 26 to 31, further comprising an additional pressure sensing element, i.e. the SAD 3203 comprises two pressure sensing elements 3204 and 3205. FIG. 32 shows a finger 3201 with artery 3202 pressing against the open surface of the SAD 3203. More pressure sensing elements could be integrated in the SAD.

The SADs disclosed in the present application operate by using the pressure between the open surface of the SAD and the finger of the subject to cause partial or total occlusion of an artery in the finger. It is assumed that the pressure to which the artery is subjected is the same as the pressure measured by the pressure sensing elements 3204 and 3205 in the SAD 3203. The accuracy of the measurement of pressure by the SAD can be reduced if there is a shear force between the finger and the SAD 3203. This shear force will cause a difference in the pressure measured by the two or more pressure sensing elements within the SAD, in particular for this embodiment, elements 3204 and 3205. The shear force can be obtained by analysing the measurements made by the two pressure sensing elements 3204 and 3205.

The estimation of the shear force can be used to increase the accuracy of estimation of the subject's BP and to reduce the magnitude of the shear force. An example of the provision of feedback to the subject based on the estimation of the shear force would be, for example, to display on the screen of a PHHCD a circle within which a spot is displayed. The position of the spot in the circle would be related to the magnitude and orientation of the measured shear force and the subject would adjust the force on the finger to move the spot towards the centre of the circle.

Pressure sensing elements 3204 and 3205 can also be used to locate the position of the artery 3202 with respect to the SAD 3203 so that, if the artery 3202 is not central, either the subject can be instructed to reposition the SAD 3203 against the body part of the subject so as to make it more central or the measured pressure can be corrected for the difference between it and the pressure at the artery 3206.

The two pressure sensing elements 3204 and 3205 in the SAD 3203 measure the pressure between the body part of the subject, e.g. finger 3201, and the SAD 3203. When the pulse reaches the artery, the artery expands and causes an increase in the pressure in the tissue of the finger 3201 surrounding the artery 3202. The magnitude of that pressure is smaller in the tissue further from the artery. Accordingly, the change in pressure measured at pressure sensing element 3204 will be greater than that measured at 3205. This difference is used to indicate whether the artery is centrally located with respect to the pressure sensing elements 3204 and 3205.

FIG. 33A to 33D show an alternative pressure sensing element. The pressure sensing element shown in FIGS. 33A to 33D can be used instead of the pressure sensing elements described in the SADs shown in FIGS. 25 to 30A-D. The alternative pressure sensing element is a MEMS pressure sensor 3300. FIG. 33A shows a cross-section of a typical MEMS pressure sensor. It is made from a block of silicon 3301 typically 1 or 2 mm wide. The surface is etched to form a thin membrane 3302. This membrane 3302 deforms when it is subject to pressure.

Four resistive elements R1, R2, R3 and R4 are embedded into the membrane 3302. The resistance of these elements changes when they are strained by the deformation of the membrane 3302. The resistance of these four resistive elements also changes with the temperature of the membrane 3302.

A common way of constructing such a device is to incorporate the four resistive elements R1, R2, R3 and R4 connected as a bridge as shown in FIG. 33B. The four resistive elements R1, R2, R3 and R4 are arranged in a square pattern around the membrane 3302. The resistors are oriented so that, when the membrane 3302 is deformed by pressure, the resistance of one pair of the elements (R1 and R4) increases and the resistance of the other pair (R2 and R3) falls. The change in differential voltage (V1−V2) is, for small changes in resistance, proportional to the average strain on the membrane.

The resistance of each element is a function of temperature and the strain to which that element is subject. Making the simplifying assumptions that the resistance of the ith resistive element is given by:

$$R_i = R_{i0}(1 + u_i T + v_i S_i)$$

where:
  $R_{i0}$ is the resistance at nominal temperature and no strain;
  T is the difference between the current temperature and the nominal temperature (assumed to be the same for all four resistive elements);
  $S_i$ is the strain of the ith resistive element;
  $u_i$ is the temperature sensitivity, where $u_i T \ll 1$; and
  $v_i$ is the strain sensitivity, where $v_i S_i \ll 1$.
The strain of the ith resistive element $S_i$ is the sum of two contributions $P + S_{gi}$ where:
  P is the average strain across the four resistive elements (proportional to the average pressure on the membrane); and
  $S_{gi}$ is the local contribution due to the difference in pressure across the MEMS pressure sensor.
Assuming that to first order the difference in pressure across the MEMS pressure sensor 3300 is expressed as:
  a strain gradient G (corresponding to the pressure difference between the two sides of the MEMS pressure sensor 3300); and
  an orientation Θ corresponding to the angle between the axis of the pressure gradient and the axis of the MEMS pressure sensor 3300
and making the simplifying assumptions that the resistance of the ith resistive element is given by:

$$R_i = R_{i0}(1 + u_i T + v_i S_i)$$

then the resistance of each of the four resistance elements can be expressed as:

$$R_1 = R_{10}(1 + u_1 T + v_1(P + G \sin \Theta))$$

$$R_2 = R_{20}(1 + u_2 T + v_2(P + G \cos \Theta))$$

$$R_3 = R_{30}(1 + u_3 T + v_3(P - G \sin \Theta))$$

$$R_4 = R_{40}(1 + u_4 T + v_4(P - G \cos \Theta))$$

u and v may be determined by calibration under controlled conditions. Therefore, there are four equations with four measured values ($R_1$ to $R_4$) that must be solved to find the four unknowns T, P, G and $\Theta$.

The difference in pressure across the MEMS pressure sensor 3300 may also be expressed to first order as two components, one aligned with one axis of the MEMS pressure sensor and the other aligned with a second axis. The transformation between this and the (G, $\Theta$) first order representation is a matter of simple trigonometry.

In practice, it is simpler to measure voltages than resistance. MEMS pressure sensors are usually manufactured as in FIG. 33C. The left and right sides may be connected together to make the simple bridge or external resistors may be added to trim out the dependence on temperature. FIG. 33D shows an arrangement where two additional resistors $R_e$ have been added and four voltages can be measured and, by application of Ohm's law, the instantaneous resistance of each of the four resistive elements $R_1$ to $R_4$ can be found. It would be more effective to measure $[(V_{ref}/2) - V_{13}]$ (and similarly for $V_{24}$) because this will have a smaller dynamic range and therefore be measured more accurately.

Hence, independent measurements of the resistance elements $R_1$, $R_2$, $R_3$ and $R_4$ of the MEMS pressure sensor 3300 are combined to make an estimate of the temperature of the membrane 3302, the average pressure to which it is subject and the orientation and magnitude of the pressure gradient across the MEMS pressure sensor.

In practice, MEMS pressure sensors are designed to minimize their sensitivity to shear force. In an alternative embodiment, the strain of each resistive element $R_1$ to $R_4$ would be determined as far as possible by the local pressure on that element with the minimum electrical coupling between the resistive elements. It would also be designed so that the change in resistance of each element with respect to strain has the same sign.

The shear force may be estimated by a measurement of the magnitude and orientation of the instantaneous pressure gradient across the MEMS pressure sensor. This measurement can be used to estimate the shear force to increase the accuracy of the measurement of the subject's blood pressure and/or temperature, to reduce the shear force and to correct for the displacement of an artery as previously disclosed.

Figure 34:
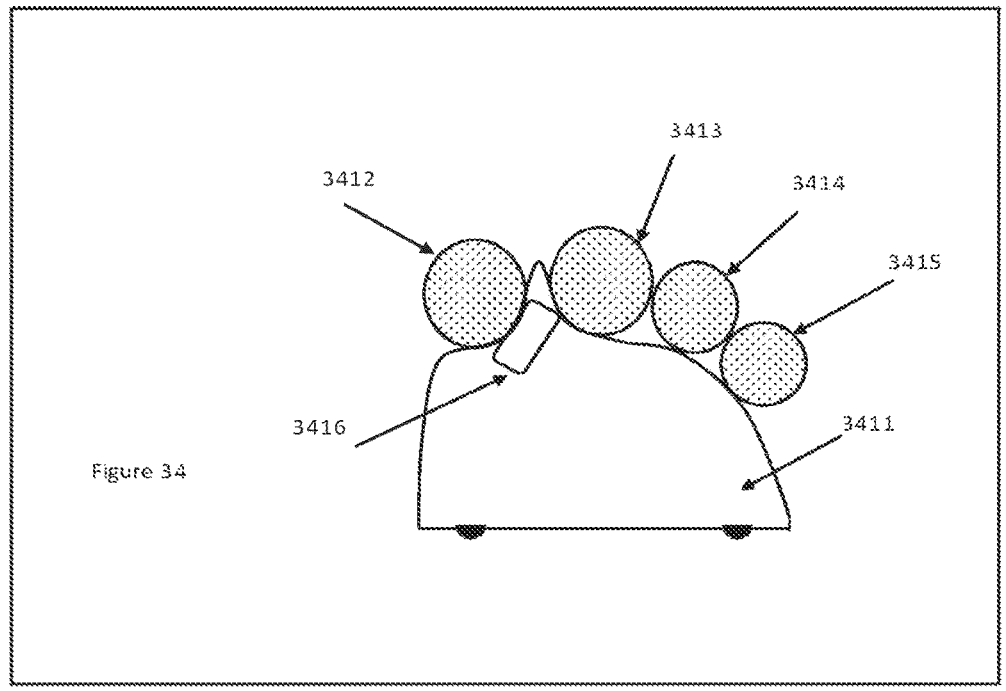
FIG. 34 shows a SAD located on a mouse.

FIG. 34 shows a cross-section through the fingers of a subject and a mouse (a computer pointing device) 3411 as part of a PHHM that comprises a computer or laptop (not shown) and a computer pointing device 3411 (i.e. the mouse), where there is the index finger 3412, middle finger 3413, ring finger 3414 and little finger 3415. The SAD 3416 of the PHHM is incorporated in the body of the computer pointing device 3411 and the index finger 3412 rests against it. The computer pointing device 3411 can be another component, such as a remote controller for a TV or other domestic electronic appliance, that could enable a measurement of subject's BP and, if desired, some other vital signs, such as a subject's blood oxygen concentration, pulse rate, respiration rate or other physiological vital signs. The SAD 3416 is adapted to transmit electrical signals to the processor of the computing system to which the mouse is connected, either by means of a cable or by wireless means such as Bluetooth.

Figure 35:
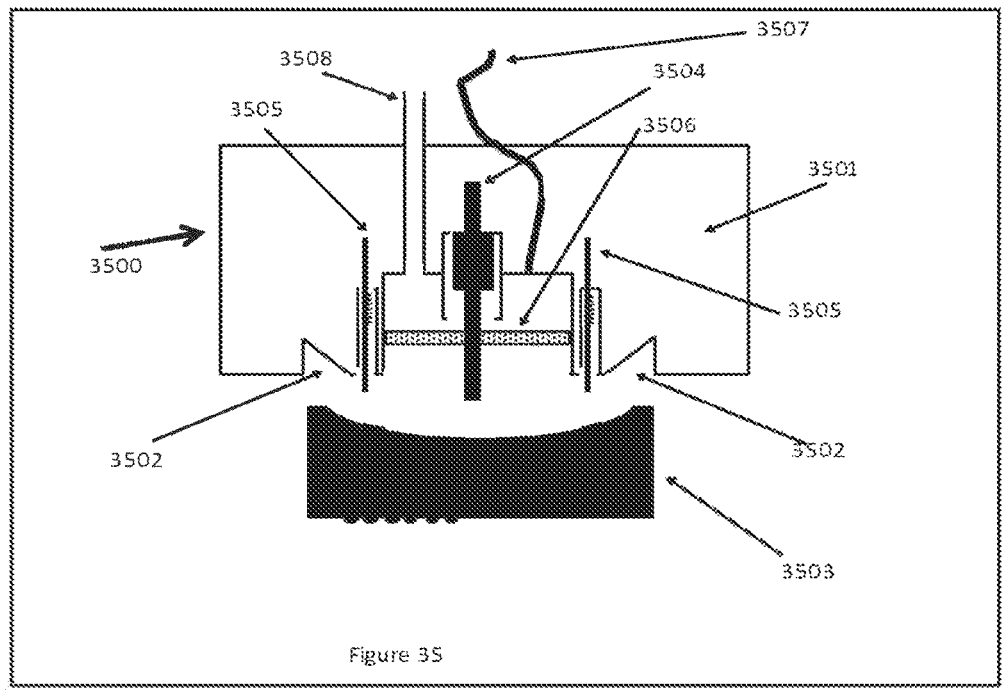
FIG. 35 shows an embodiment of a holder.

FIG. 35 shows an embodiment of a holder 3500 according to an aspect of the present invention. The holder 3500 is equipped to check that a SAD 3503 under test is functioning correctly before it is calibrated. FIG. 35 shows a sketch of a cross-section of the holder. The SAD 3503 under test is held against the holder body 3501 by a partial vacuum through pipe 3508. In FIG. 35, the SAD 3503 is shown displaced downwards to make the components clearer; in use, it is engaged into the shape of the underside of the holder, indicate by the two cut-outs 3502.

Figure 3:
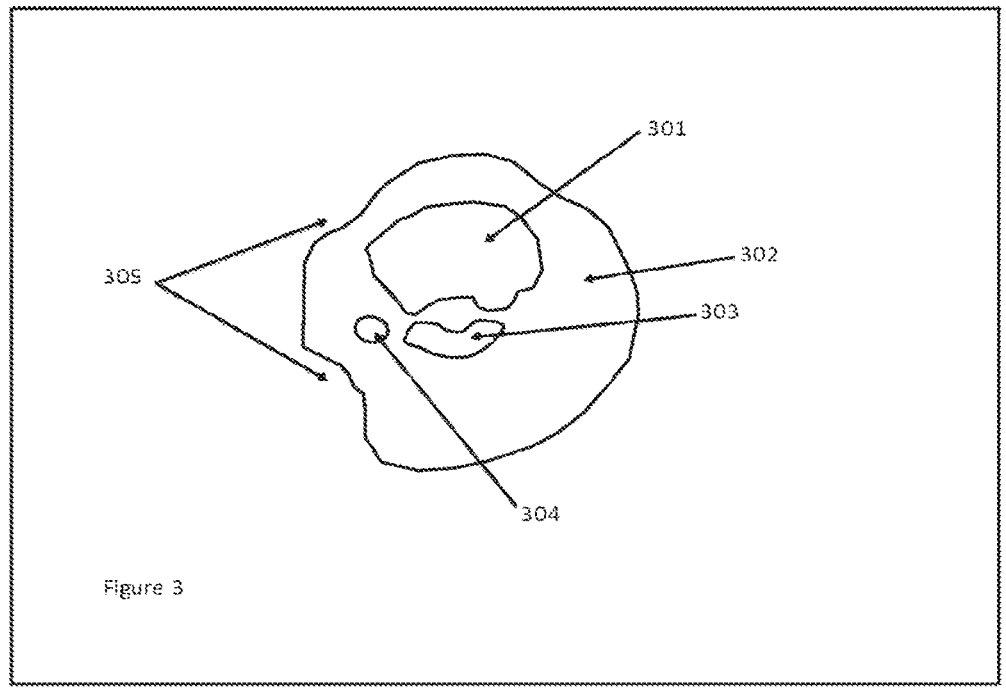
FIG. 3 is sketched from a Magnetic Resonance Image of a finger pressed against a SAD.
Figure 4:
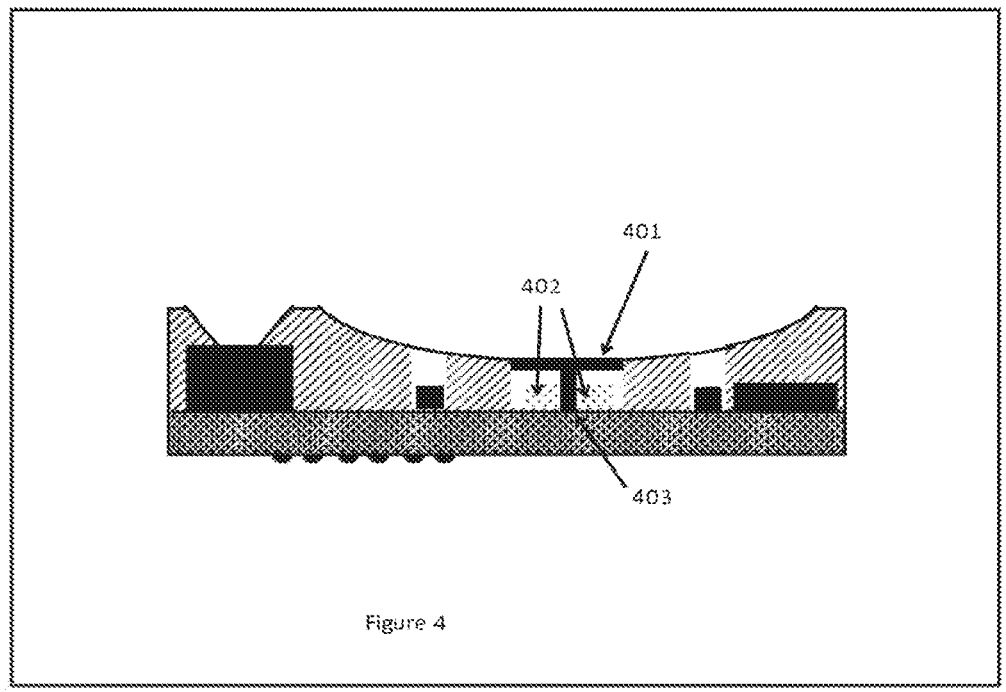
FIG. 4 is a representation of a SAD incorporating a magnetic pressure sensor.
Figure 5:
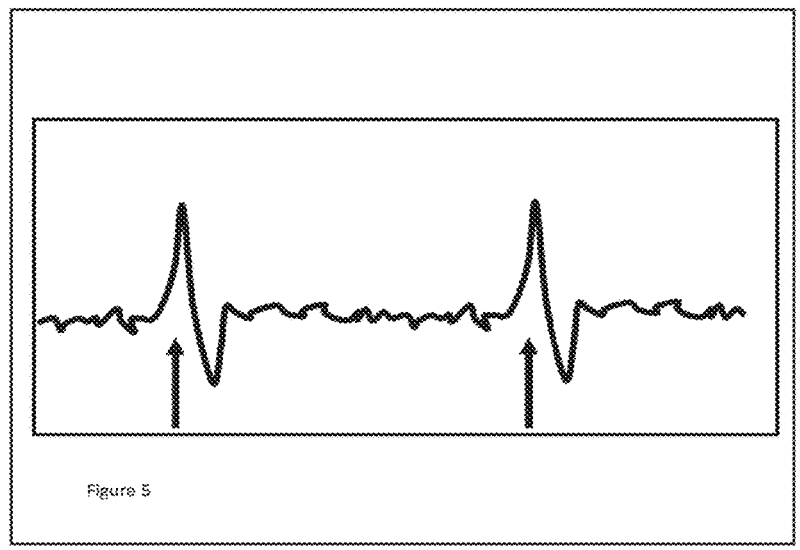
FIG. 5 is a representation of the electrical signals measured by a SAD.
Figure 6:
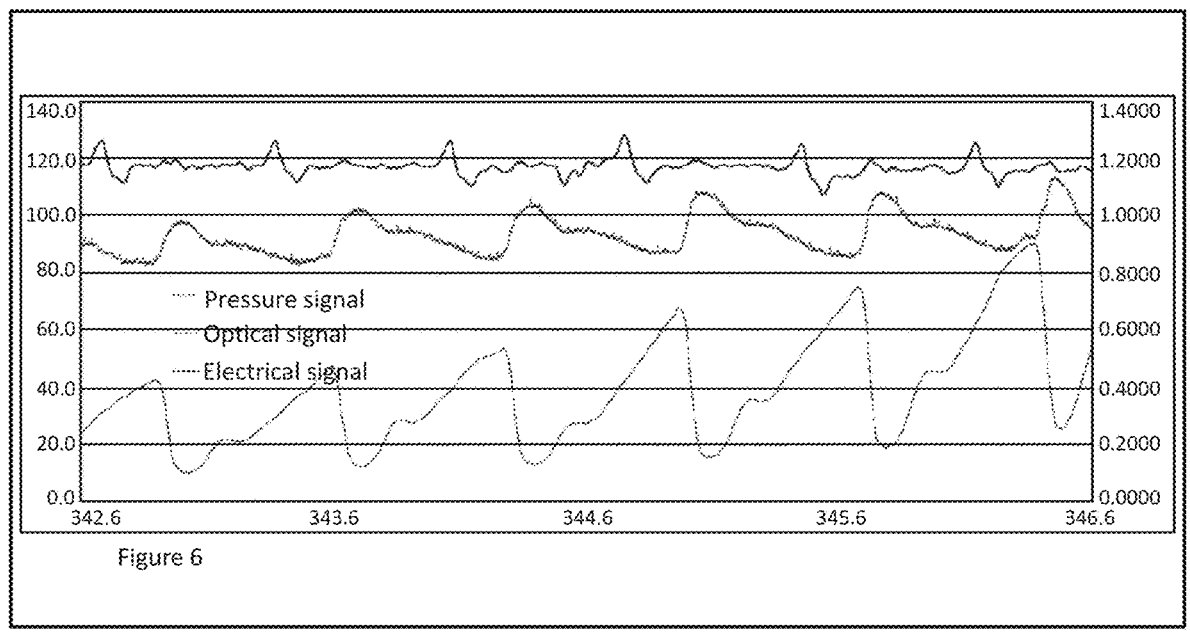
FIG. 6 shows the waveforms of typical signals received from optical, pressure and electrical sensors of a SAD.
Figure 7:
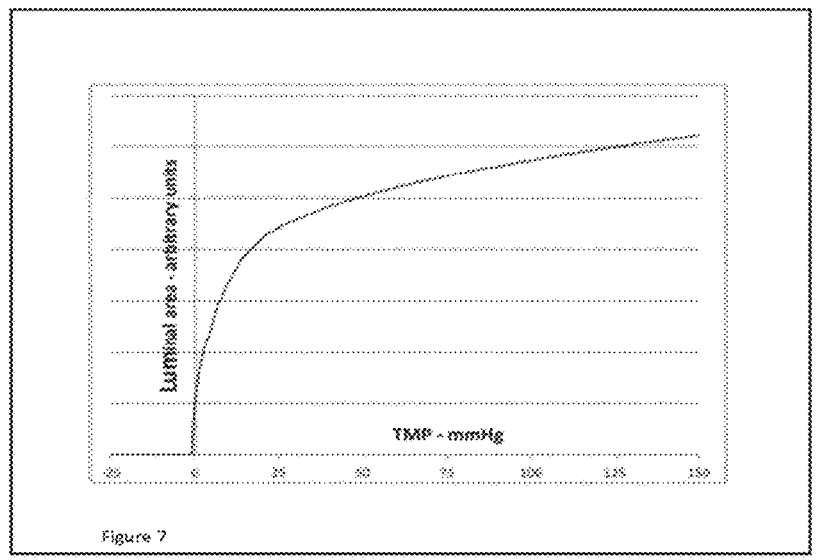
FIG. 7 shows the typical relationship between luminal area and pressure.
Figure 8:
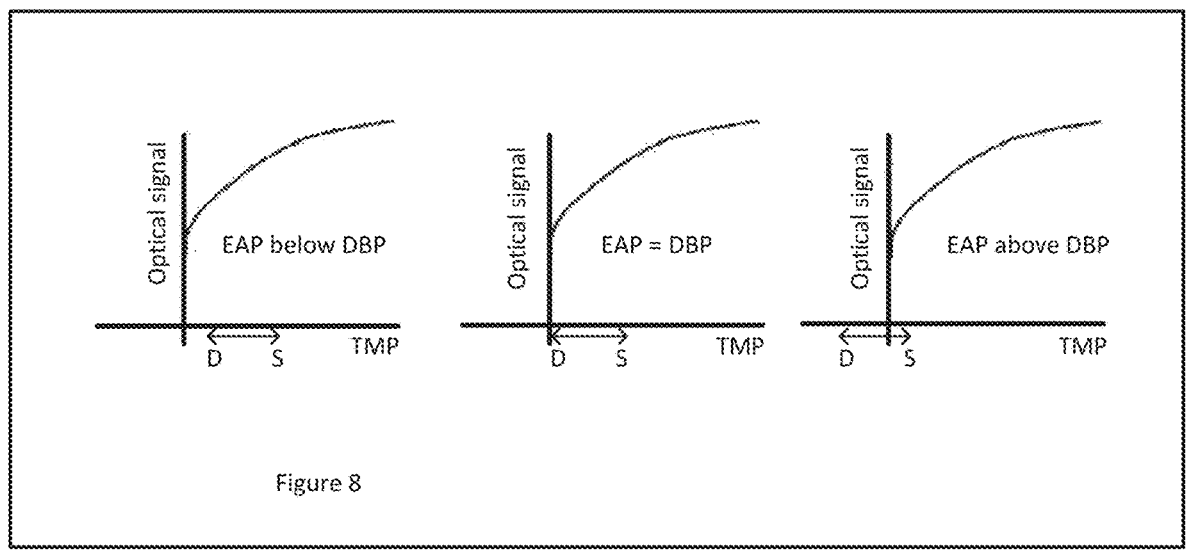
FIG. 8 shows a range of pressures encountered during the arterial cycle at various External Applied Pressures.
Figure 9:
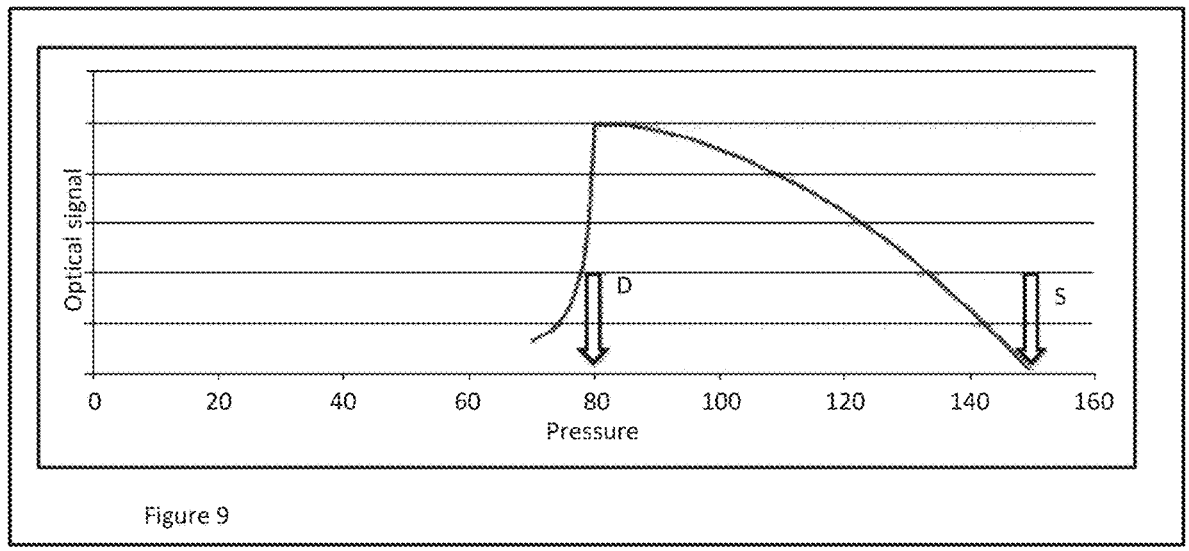
FIG. 9 shows a simulation of the difference between the luminal area at systole and diastole as a function of EAP.
Figure 10:
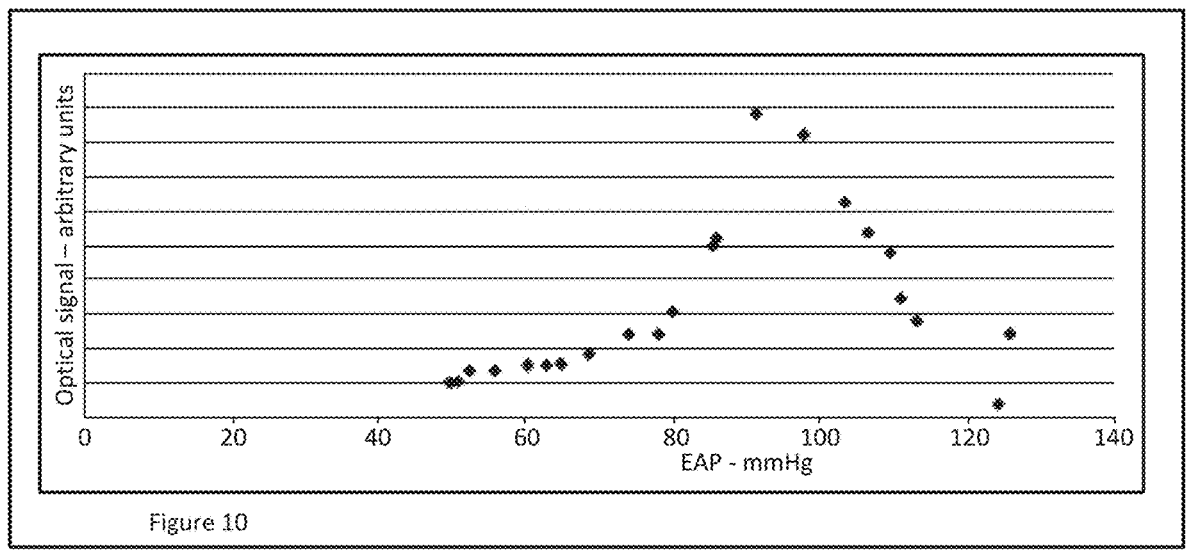
FIG. 10 shows a measured version of the simulated curve of FIG. 9.
Figure 11:
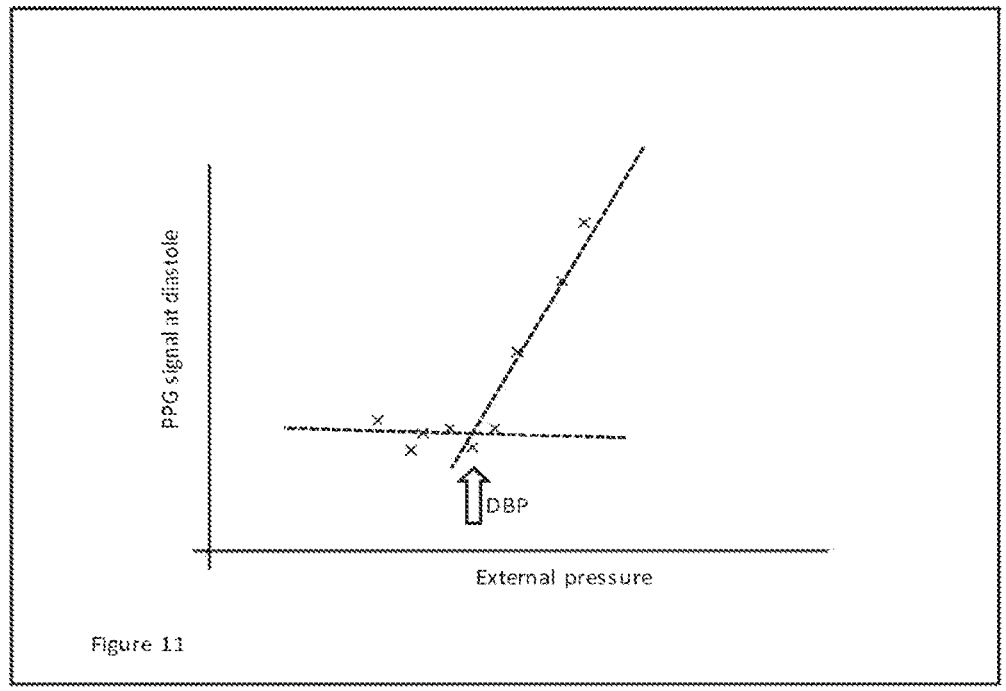
FIG. 11 shows a plot of the absolute PPG signal at diastole against the measured external pressure.
Figure 12:
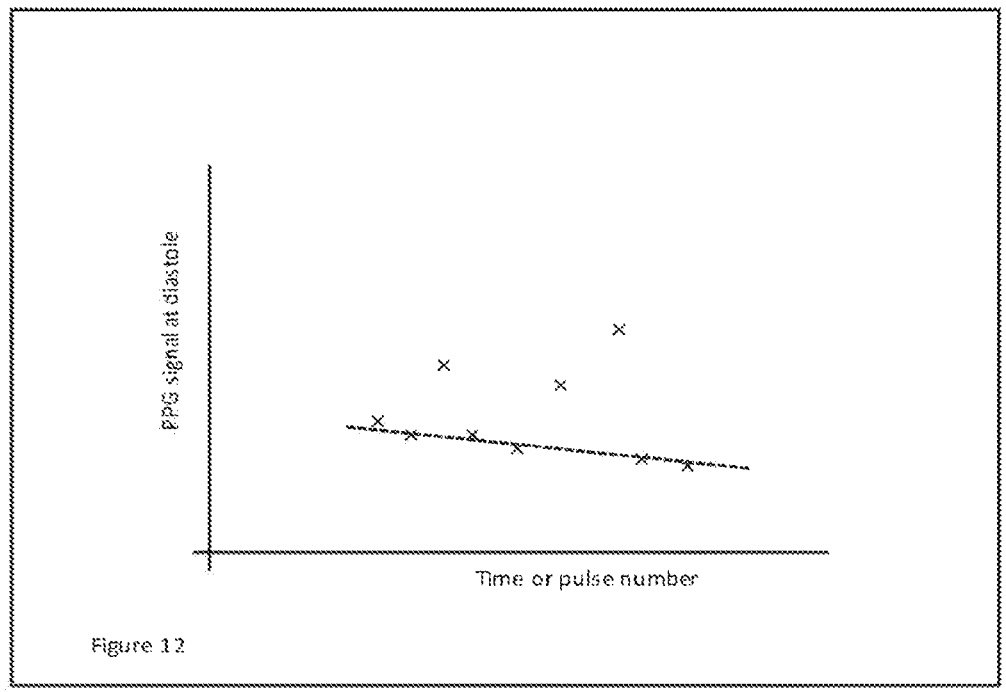
FIG. 12 shows the plot of FIG. 11 against time.
Figure 13:
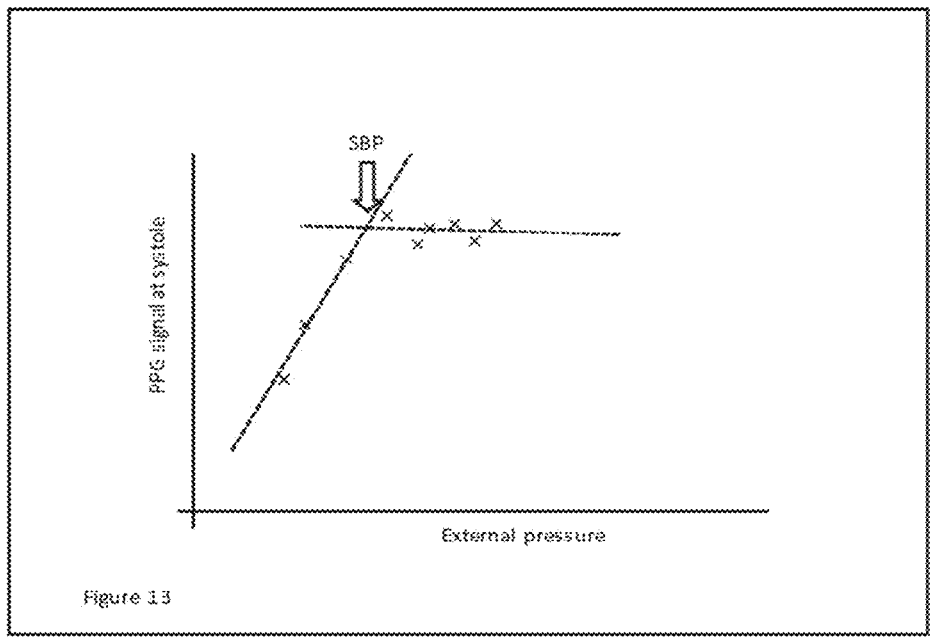
FIG. 13 shows a plot of the absolute PPG signal at systole against the measured external pressure.
Figure 14:
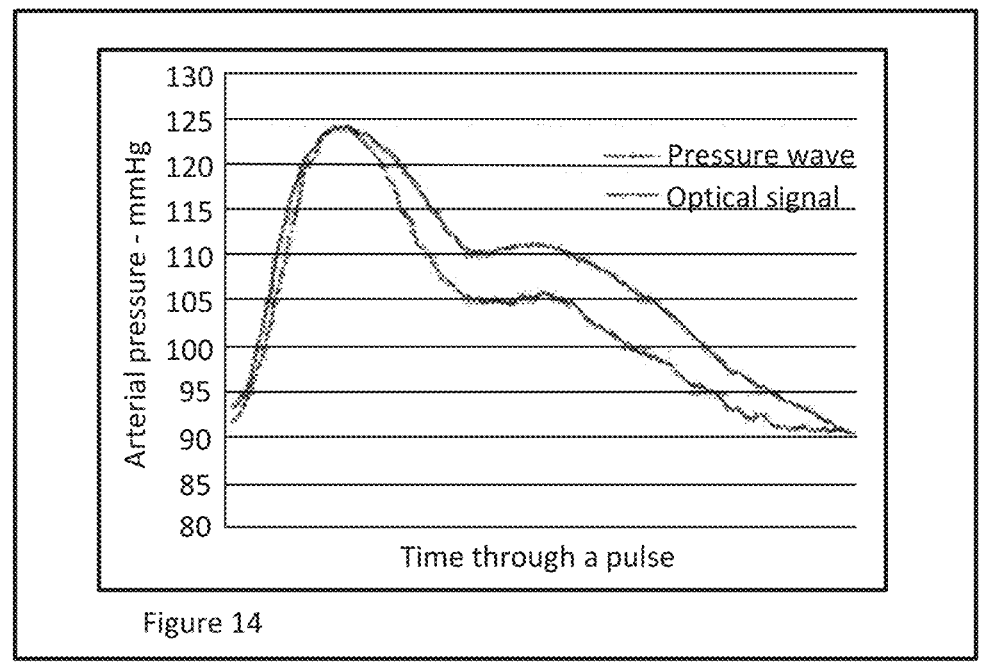
FIG. 14 shows the instantaneous arterial pressure.
Figure 15:
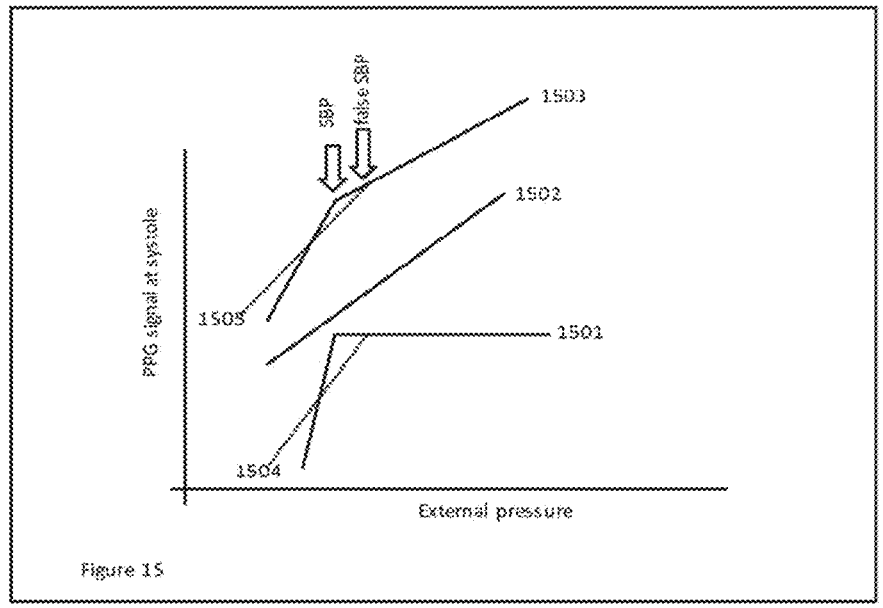
FIG. 15 shows the components of FIG. 13.
Figure 16:
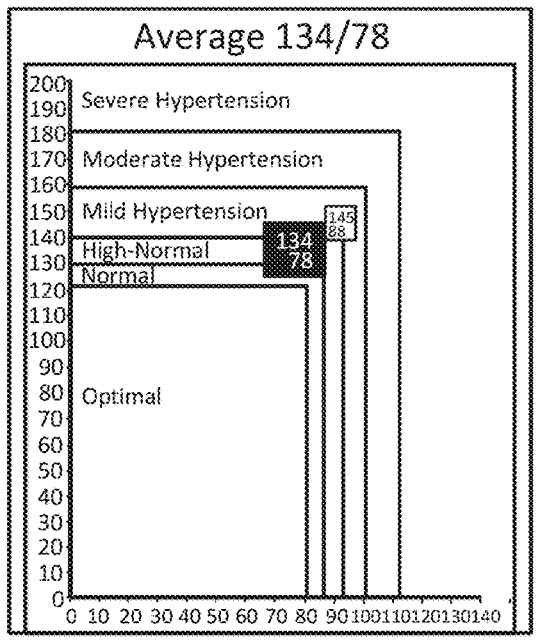
FIGS. 16 and 17 show embodiments of the display of the blood pressure results.
Figure 17:
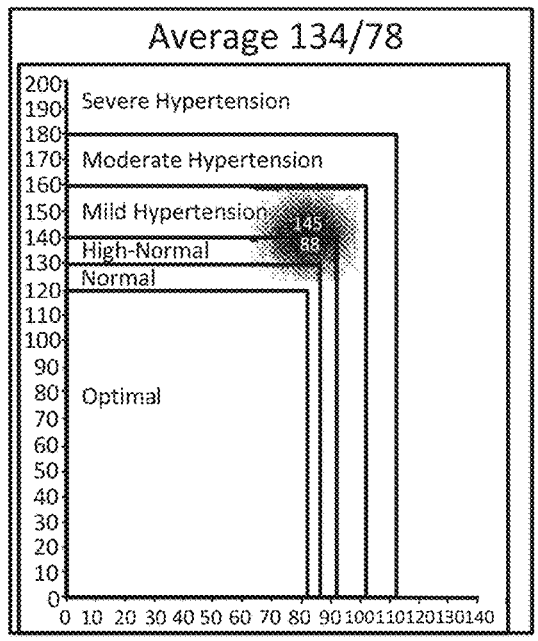
Figures 18A, 18B:
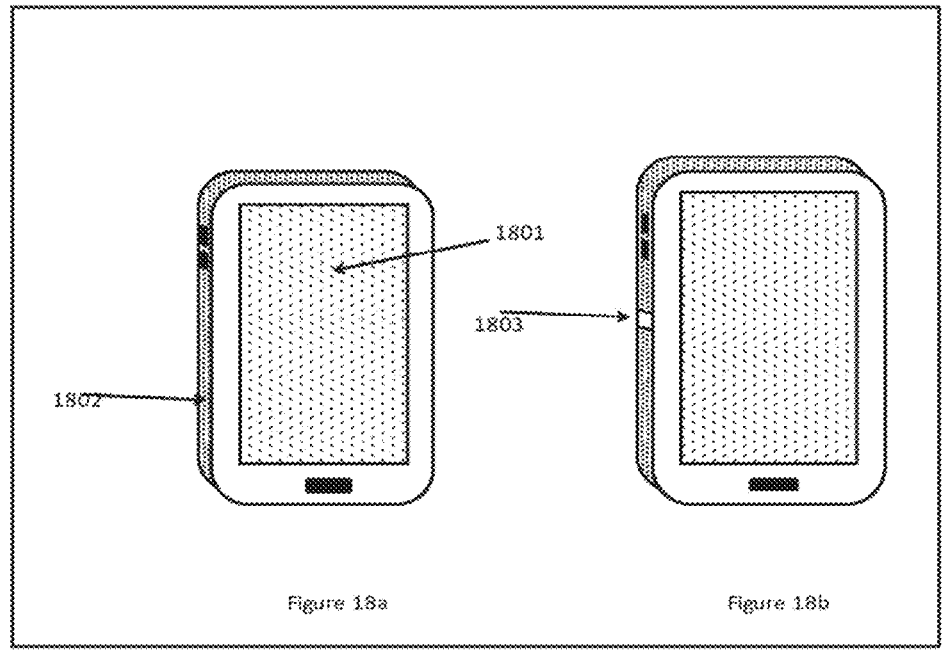
FIG. 18A shows a band around a typical smartphone.
FIG. 18B shows a break in the band shown in FIG. 18A to form two electrodes.
Figure 19:
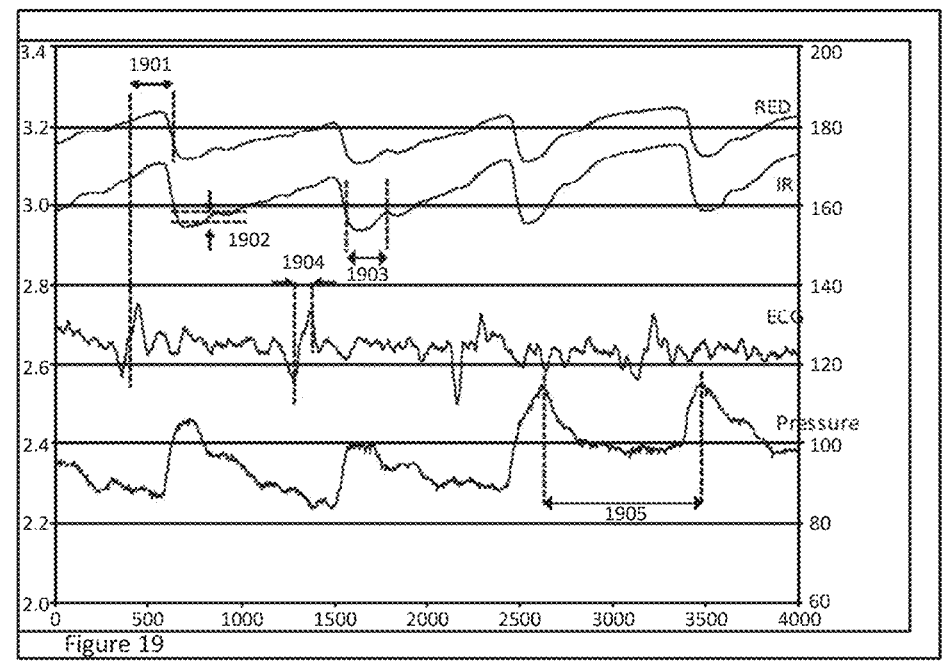
FIG. 19 shows typical data recorded from a SAD.
Figure 20:
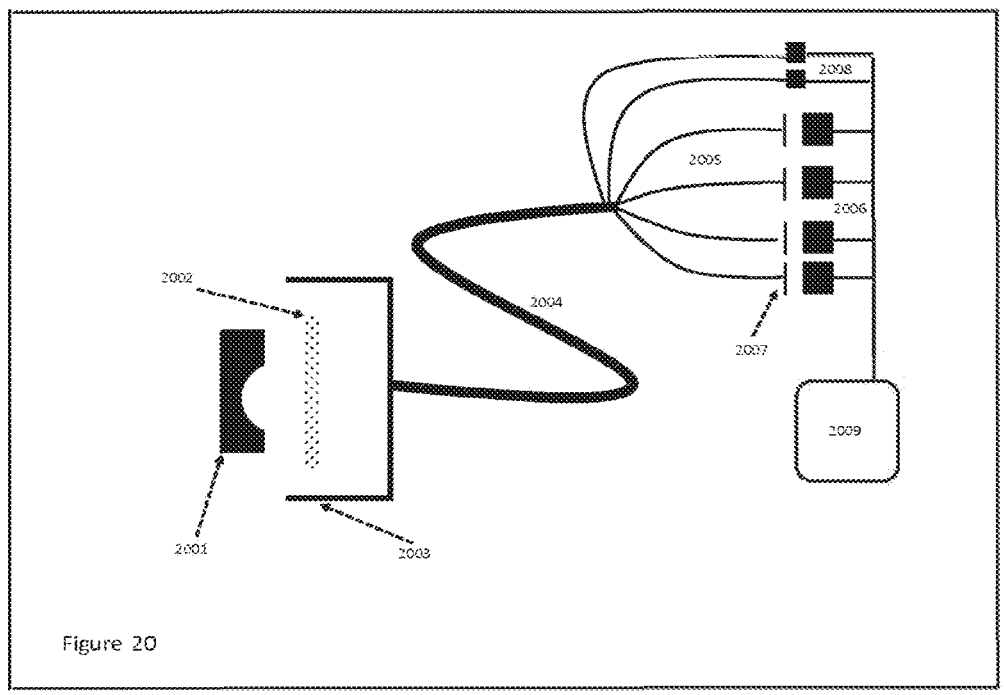
FIG. 20 shows a possible optical configuration of a holder.
Figure 21:
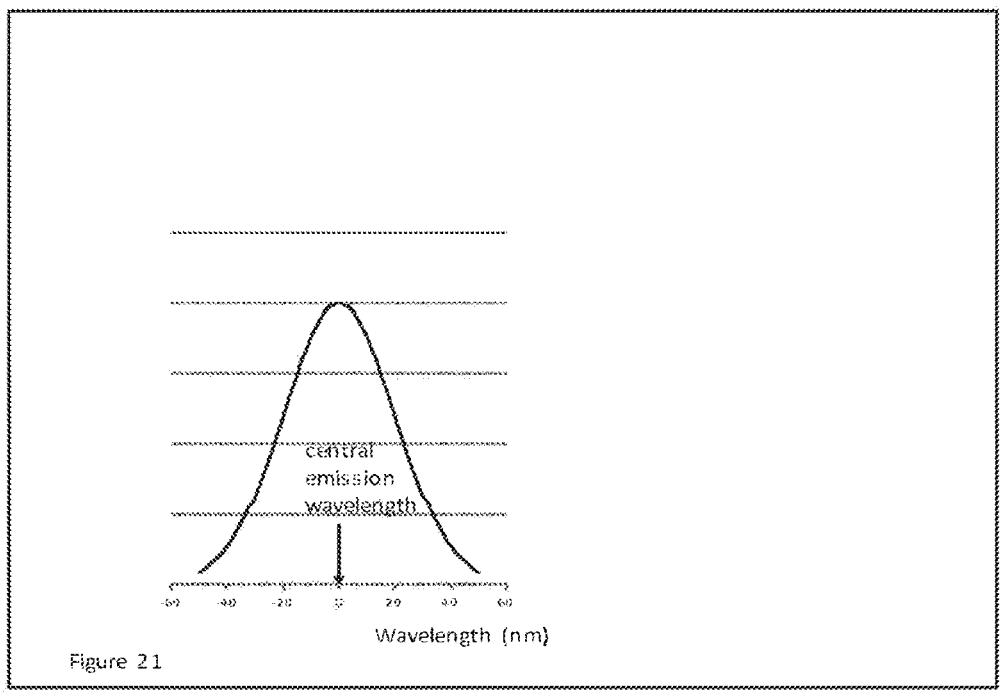
FIG. 21 shows the typical spectral response of an inexpensive red LED.
Figure 22:
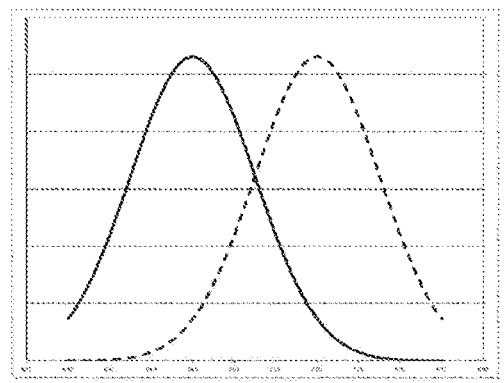
FIG. 22 shows the typical spectral response of the two filters used to analyse an inexpensive red LED.
Figure 23:
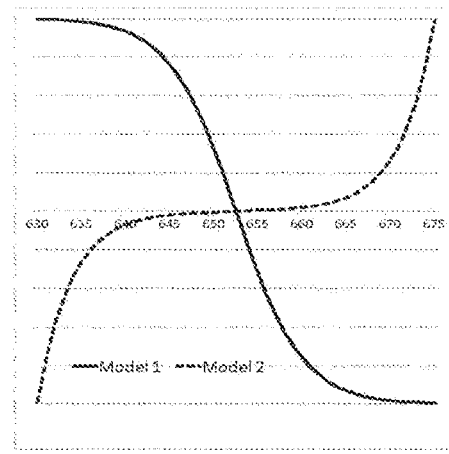
FIG. 23 shows the relative value of the signals from two photo-detectors.
Figure 24:
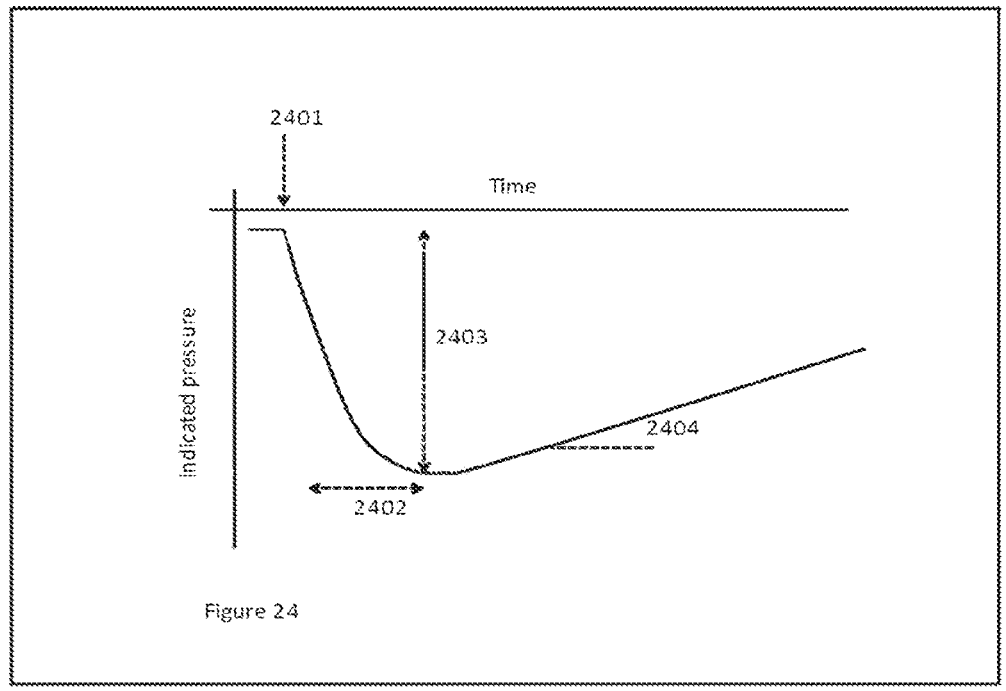
FIG. 24 shows a typical response to LED heating.

The holder 3500 comprises the fibre optic cable 3507 (as 2004 in FIG. 20) and the optical diffuser 3506 (as 2002 in FIG. 20). One or more spring-loaded connectors 3505 in the holder presses on the pad(s) (not shown) on the open surface of the SAD 3503 and permits the testing of the SAD through the calibration board. A spring-loaded probe 3504 is adapted to rest on the open surface in contact with the flexible and essentially incompressible gel (not shown) and the pressure signal is measured by the circuits of the calibration board. The pressure signal may be used to confirm that the pressure sensor of the SAD 3503 is functional and to make an estimate of its sensitivity. The signal from the probe 3504 measures the height of the essentially incompressible gel with respect to the open surface of the SAD 3503.

The same, or a similar, holder is also used to remove the SAD 3503 from the calibration board after calibration. The tests are repeated to check that the module has not failed during calibration. The test of the height of the essentially incompressible gel is repeated because the calibration of the pressure sensor is known after calibration and so the height of the essentially incompressible gel can be estimated more accurately. The holder 3500 is equipped with a mechanism (not shown in FIG. 35) to release mechanical retaining clips 3601 shown in FIG. 36 that hold the SAD 3503 under test to the socket within the calibration board and to remove the SAD 3503 using the partial vacuum to retain it against the holder 3500.

Figure 36:
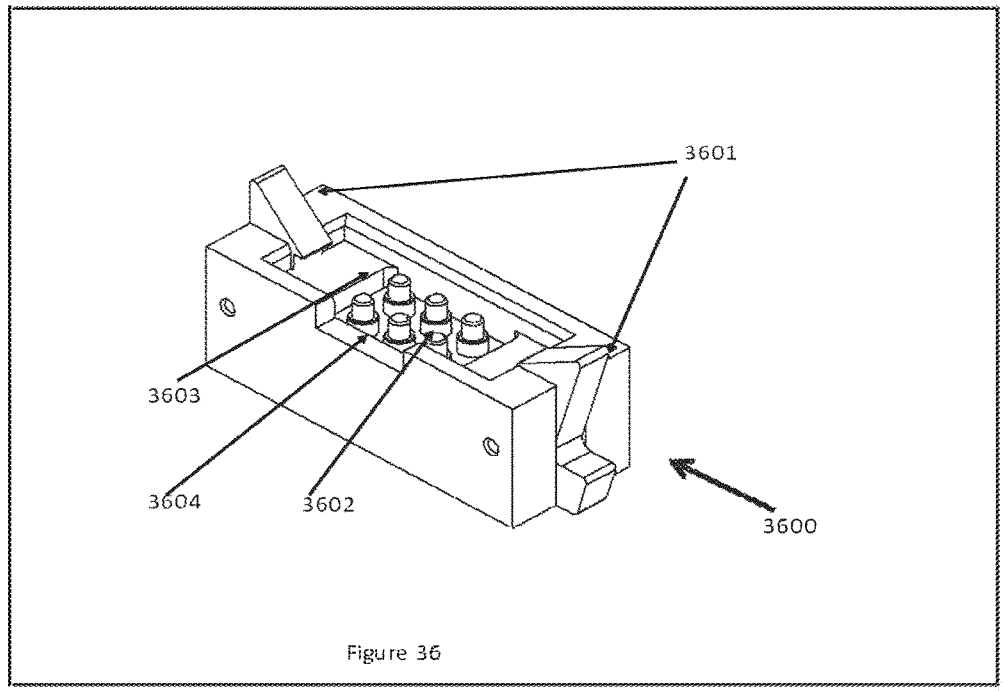
FIG. 36 shows an embodiment of a socket.

The SAD 3503 is inserted in a socket shown in FIG. 36 on the calibration board. FIG. 36 shows a socket 3600 to be used on the calibration board to hold and connect to each SAD under calibration test. FIG. 36 is a sketch of the socket 3600. There are spring-loaded connecting pins 3602 that press against the connectors of the SAD. The SAD is retained by mechanical retaining clips 3601 that snap into slots of the type shown in FIG. 29 in the side of the housing of the SAD. The SAD is located on a well 3603 that is slightly larger than the base of the SAD. A cut-out 3604 is provided in the side of the well in case it is necessary to test the SAD with their flexible connectors already attached. In this case, the pins 3602 press on flexible connector.

The socket provides electrical connections between an external computer and the SAD under test.

Figure 37:
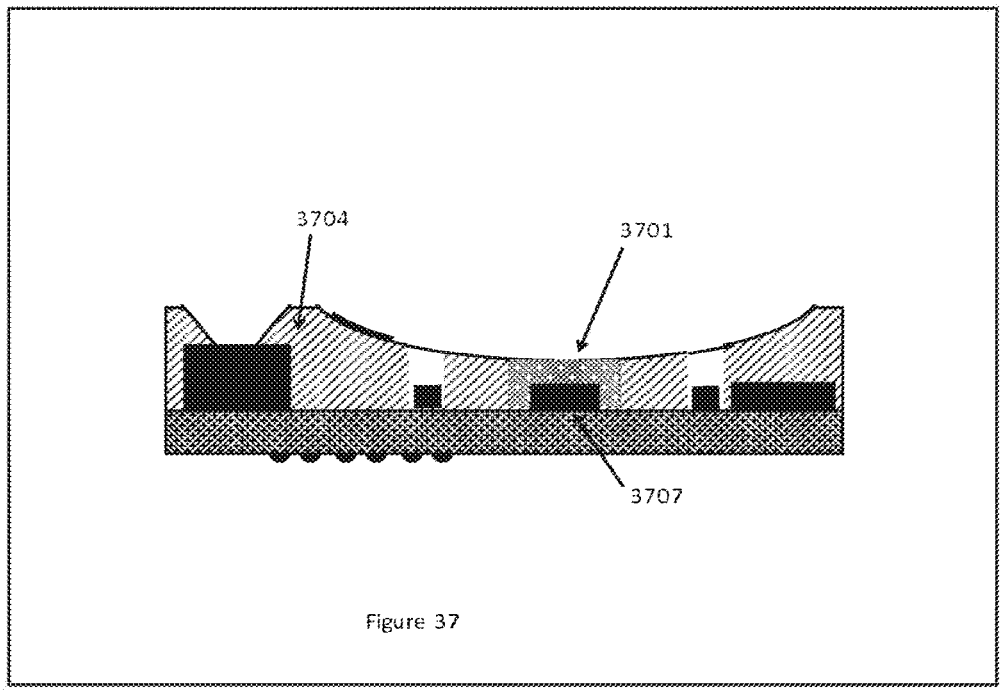
FIG. 37 shows an embodiment of a SAD and the location of a gel.

FIG. 37 shows a SAD comprising a gel 3701 surrounding a pressure sensor 3707 within a housing 3704. The gel consists of a flexible epoxy resin formed from EPICOL 295, a 2-component system for making a soft epoxy resin including a modified epoxy resin and a modified amine hardener, supplier by APM Technica. The hardened resin has a Durometer, measured on the Shore A scale at 25° C., of 60.

In an alternative embodiment, the gel consists of a cured silicone resin formed from Dow Corning Sylgard 160, a 2 component system for making a soft silicone resin including a silicone resin and a catalyst. The cured resin has a Durometer, measured on the Shore A scale at 25° C., of 56.

In other respects, the SAD is identical to the SADs described above.

The SAD as described above was incorporated into a cellphone such that the sensors in the SAD can receive signals from and transmit signals to the processor of the cellphone. The processor of the cellphone was programmed such that it can operate in accordance with all of the aspects of the present invention described above.

In an alternative embodiment, the SAD was incorporated into a pointing device (a mouse) connected by wire or wirelessly to a personal computer such that the sensors in the SAD can receive signals from and transmit signals to the processor of the personal computer via the pointing device. The processor of the personal computer was programmed such that it can operate in accordance with all of the aspects of the present invention described above.

The present invention has been described above by way of example only. The invention is not limited to the disclosures made above and is only limited by the spirit and scope of the invention as determined by the attached claims.

The invention claimed is:

1. A system, comprising:
   a processor; and
   a signal acquisition device (SAD), the SAD comprising:
      a blood flow occlusion device having an open surface available to be pressed against a body part of the subject or to have a body part of the subject pressed against it;
      a pressure sensor adapted to provide an electrical signal indicative of the pressure applied to or by the open surface;
      an optical blood flow detecting device configured to detect the flow of blood in the body part of the subject when pressure is applied to or by the open surface; and
      a device configured to: receive electrical signals from the pressure sensor and the optical blood flow detecting device and to transmit electrical signals indicative of the pressure and blood flow to the processor,
   wherein the processor is configured to provide at least a measurement of the diastolic blood pressure (DBP) and systolic blood pressure (SBP) of the subject using a non-linear parametric function that predicts optical signals, and wherein the subject's DBP and SBP values are estimated by:
      using the parametric functions to generate predicted optical signals from one or more candidate DBP and SBP values;
      comparing the predicted optical signals to the measured optical signals; and
      adjusting the candidate DBP and SBP values to find the candidate DBP and SBP values that minimize the difference between the predicted optical signals and the measured optical signals, and using those candidate DBP and SBP values as the estimate of the subject's DBP and SBP values.

2. The system of claim 1, wherein the processor is adapted to measure the gradient of the absolute optical signal at systole as a function of the measured external pressure and to use the said slope in order to estimate the error due to a misplaced body part.

3. The system of claim 1, wherein the processor is adapted to measure the relative amplitude of red and infrared optical signals as a function of the pressure measured by the pressure sensor and to use said ratio to estimate the error due to a misplaced body part.

4. The system of claim 1, wherein the processor is adapted to derive from the measured pressure and optical signals estimates of the degree to which the body part is misplaced.

5. The system of claim 4, wherein the processor is adapted to use estimates of the degree to which the body part is misplaced to estimate and correct for the error in the estimated SBP and/or DBP due to the misplacing of the body part.

6. The system of claim 4, wherein the error in the measured SBP is used to estimate and correct for the error in the measured DBP or vice versa.

7. The system of claim 1, wherein the processor is adapted to use said gradient to determine if the body part is so misplaced as to render resulting estimates of SBP and DBP unreliable and to warn the user by way of audible and/or visual signals.

8. The system of claim 1, wherein the PHHM is further adapted to generate a correction factor based on the relative locations of the body part of the subject and the blood flow occlusion device, wherein said correction factor is used to increase the accuracy of estimation of the value of BP.

9. The system of claim 1, wherein a genetic algorithm is adapted to carry out the generating and comparing, and to do so repetitively for a fixed number of repetitions.

10. The system of claim 9, wherein the genetic algorithm is adapted to carry out generating and comparing repetitively until a desired minimized different is achieved.

11. The system of claim 1, wherein the non-linear parametric function predicts optical signals from a decay law of optical intensity.

12. A method for estimating a subject's DBP and SBP, comprising:
   receiving electrical signals indicative of the subject's pressure and blood flow;
   providing at least a measurement of the diastolic blood pressure (DBP) and systolic blood pressure (SBP) of the subject using a non-linear parametric function that predicts optical signals from a decay law of optical intensity, wherein the subject's DBP and SBP values are estimated by:
      using the parametric functions to generate predicted optical signals from one or more candidate DBP and SBP values;
      comparing the predicted optical signals to the measured optical signals; and
      adjusting the candidate DBP and SBP values to find the candidate DBP and SBP values that minimize the different between the predicted optical signals and the measured optical signals, and using those candidate DBP and SBP values as the estimate of the subject's DBP and SBP values.

* * * * *